United States Patent
Bordey et al.

(10) Patent No.: US 12,274,756 B2
(45) Date of Patent: Apr. 15, 2025

(54) METHODS OF TREATING AND DIAGNOSING EPILEPSY

(71) Applicant: YALE UNIVERSITY, New Haven, CT (US)

(72) Inventors: Angelique Bordey, Guilford, CT (US); Lawrence Hsieh, West Hartford, CT (US); Jianbing Zhou, New Haven, CT (US)

(73) Assignee: Yale University, New Haven, CT (US)

( * ) Notice: Subject to any disclaimer, the term of this patent is extended or adjusted under 35 U.S.C. 154(b) by 834 days.

(21) Appl. No.: 17/436,165

(22) PCT Filed: Mar. 4, 2020

(86) PCT No.: PCT/US2020/020994
§ 371 (c)(1),
(2) Date: Sep. 3, 2021

(87) PCT Pub. No.: WO2020/180990
PCT Pub. Date: Sep. 10, 2020

(65) Prior Publication Data
US 2022/0143219 A1    May 12, 2022

Related U.S. Application Data

(60) Provisional application No. 62/813,429, filed on Mar. 4, 2019.

(51) Int. Cl.
| | | |
|---|---|---|
| A61K 48/00 | (2006.01) | |
| C12N 9/22 | (2006.01) | |
| C12N 15/11 | (2006.01) | |
| C12N 15/113 | (2010.01) | |

(52) U.S. Cl.
CPC ........ *A61K 48/0016* (2013.01); *A61K 48/005* (2013.01); *C12N 9/22* (2013.01); *C12N 15/111* (2013.01); *C12N 15/1138* (2013.01); *C12N 2310/20* (2017.05)

(58) Field of Classification Search
CPC ............... A61K 48/005; C12N 15/111; C12N 15/1138; A61B 5/4094; G01N 2800/2857
See application file for complete search history.

(56) References Cited

U.S. PATENT DOCUMENTS

2004/0115668 A1    6/2004 Folander

FOREIGN PATENT DOCUMENTS

| WO | 2011000915 A1 | 1/2011 |
| WO | 2018196782 A1 | 11/2018 |

OTHER PUBLICATIONS

Yehia and Eng, "PTEN Hamartoma Tumor Syndrome" Updated Feb. 1, 2021, In: Adam, et al., GeneReviews® (Year: 2021).*
Hsieh et al., Jun. 1, 2016, "Convulsive seizures from experimental focal cortical dysplasia occur independently of cell misplacement" Nature Communications, 7:11753, p. 1-12 (Year: 2016).*
Andresen et al., 2014, "Gabapentin attenuates hyperexcitability in the freeze-lesion model of developmental cortical malformation" Neurobiology of Disease, (2014), p. 305-316 (Year: 2014).*
Tae et al., Aug. 21, 2017, "Gabapentin Modulates HCN4 Channel Voltage-Dependence" Frontiers in Pharmacology, 8:554, p. 1-13 (Year: 2017).*
Günther et al., Dec. 25, 2018, "HCN4 knockdown in dorsal hippocampus promotes anxiety-like behavior in mice" Genes, Brain and Behavior, 2019; 18:312550 (Year: 2018).*
Surges et al., 2012, "Hyperpolarization-activated cation current Ih of dentate gyrus granule cells is upregulated in human and rat temporal lobe epilepsy" Biochemical and Biophysical Research Communications, 420 (2012), p. 156-160 (Year: 2012).*
Chen et al., 2017, "Targeted Delivery of CRISPR/Cas9-Mediated Cancer Gene Therapy via Liposome-Templated Hydrogel Nanoparticles" Advanced Functional Materials, 27, 1703036, p. 1-9 (Year: 2017).*
Parsons et al., Dec. 13, 2006, "Translational Control via the Mammalian Target of Rapamycin Pathway Is Critical for the Formation and Stability of Long-Term Fear Memory in Amygdala Neurons" The Journal of Neuroscience, 26(50): p. 12977-12983 (Year: 2006).*
Saxton and Sabatini, Mar. 9, 2017, "mTOR Signaling in Growth, Metabolism, and Disease" Cell, 168, p. 1-29 (Year: 2017).*
Peters et al., Jun. 20, 2022, "Regulation of HCN Channels by Protein Interactions" Frontiers in Physiology, 13:928507, p. 1-10 (Year: 2022).*
Servatius et al., 2018, "Phenotypic Spectrum of HCN4 Mutations" Circ Genom Precis Med, 2018;11:e002033 (Year: 2018).*
Mesirca et al., Aug. 21, 2014, "Cardiac arrhythmia induced by genetic silencing of 'funny' (f) channels is rescued by GIRK4 inactivation" Nature Communications, 5:4664, p. 1-15 and Supplementary Information (Year: 2014).*
Seo et al., Feb. 27, 2015, "Differential expression of hyperpolarizationactivated cyclic nucleotide-gated channel subunits during hippocampal development in the mouse" Molecular Brain, (2015) 8:13, p. 1-14 (Year: 2015).*
"P-glycoprotein Inhibition as Adjunct Treatment for Modically Refractory Cpilepsy", Clinical Trials.gov, (20100520), pp. 1-8.
Amin, Md Lutful. "P-glycoprotein inhibition for optimal drug delivery." Drug target insights 7 (2013): DTI-S12519. 8 pages.
Cao, Ying, et al. "Inhibition of hyperpolarization-activated cyclic nucleotide-gated channels by β-blocker carvedilol." British Journal of Pharmacology 175.20 (2018): 3963-3975.

(Continued)

*Primary Examiner* — Jennifer Dunston
*Assistant Examiner* — Jenna L Persons
(74) *Attorney, Agent, or Firm* — Saul Ewing LLP; Justin Crotty

(57) ABSTRACT

In various aspects and embodiments the invention provides a method of treating epilepsy in a subject in need thereof, the method comprising contacting a target cell of the subject with an effective amount of an HCN4 disrupting agent.

8 Claims, 17 Drawing Sheets

Specification includes a Sequence Listing.

(56) References Cited

OTHER PUBLICATIONS

Günther, Anne, et al. "HCN4 knockdown in dorsal hippocampus promotes anxiety-like behavior in mice." Genes, brain and behavior 18.2 (2019): e12550. 12 pages.

* cited by examiner

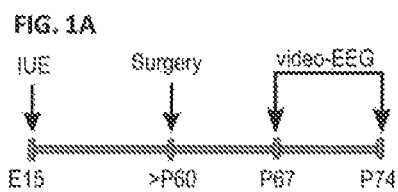
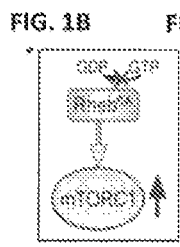
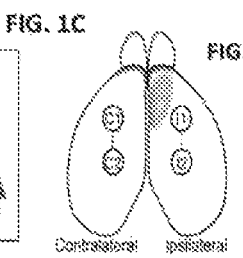
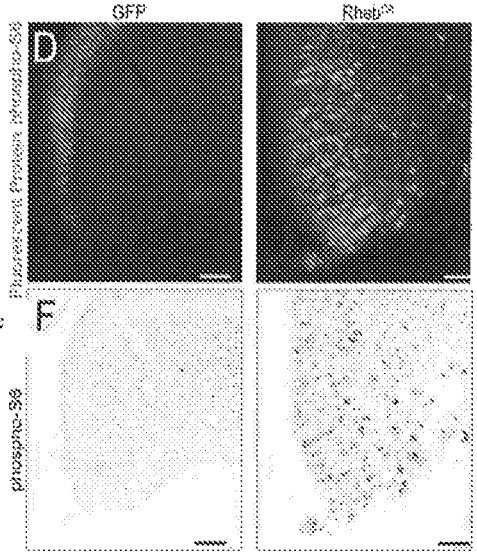
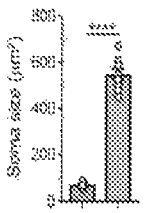
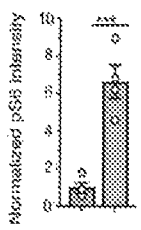
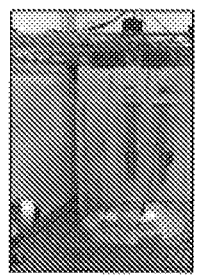
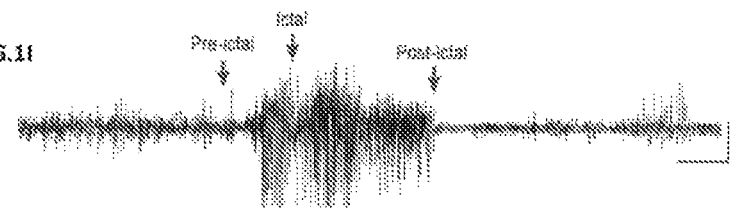
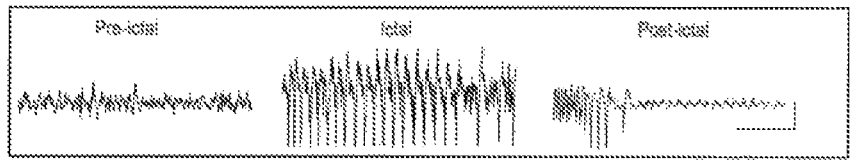

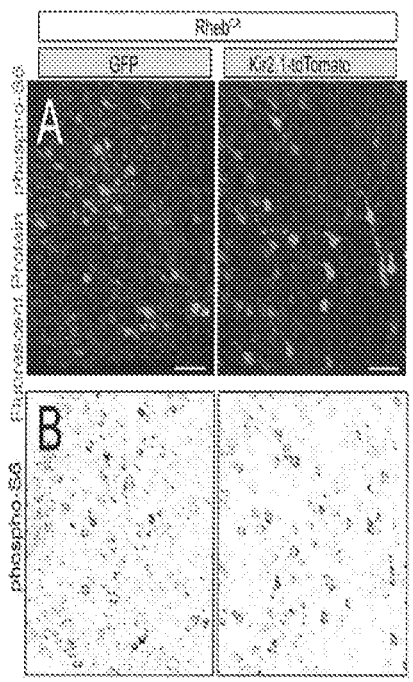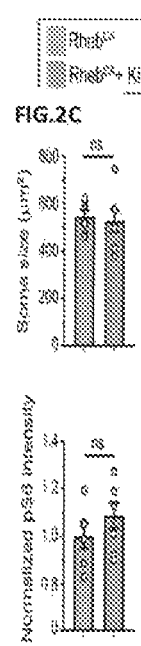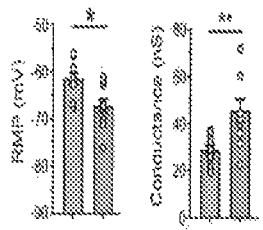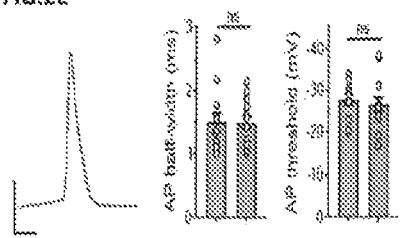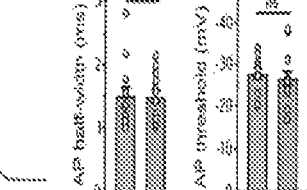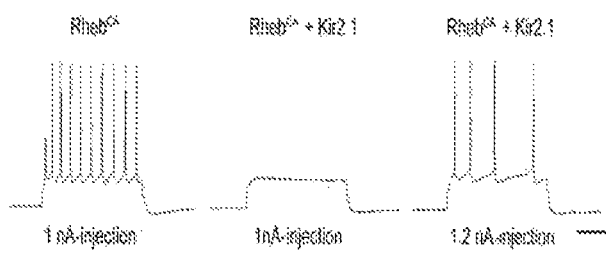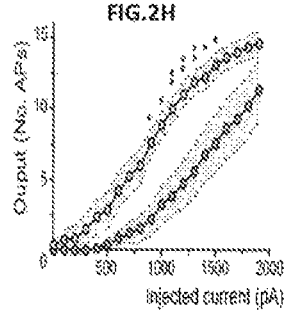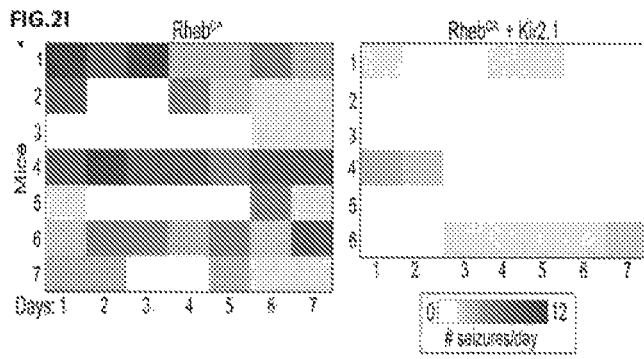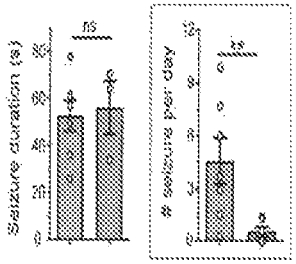

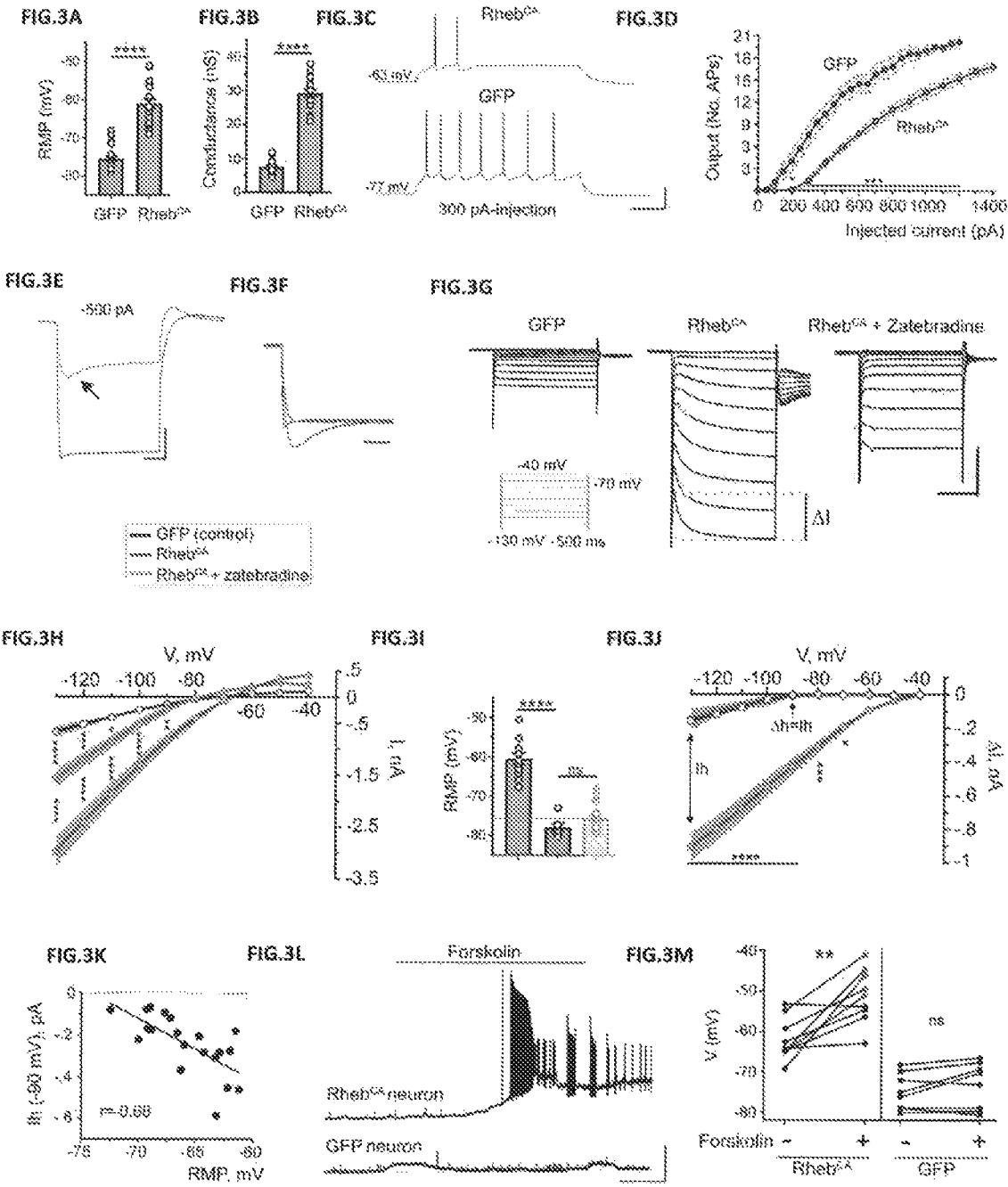

FIG. 4A 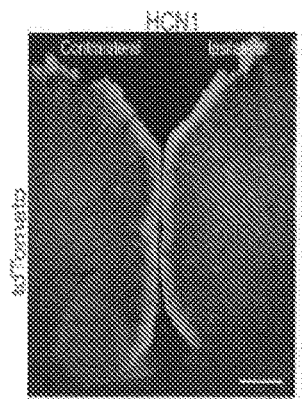 FIG. 4B 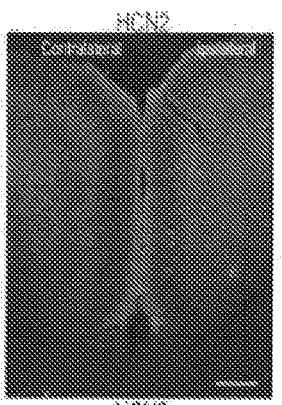 FIG. 4C 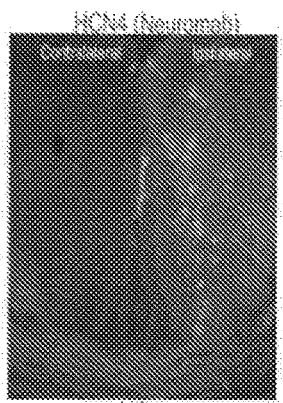 FIG. 4D 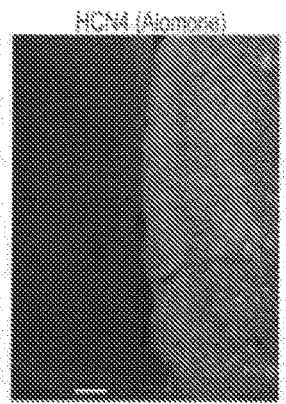
FIG. 4E 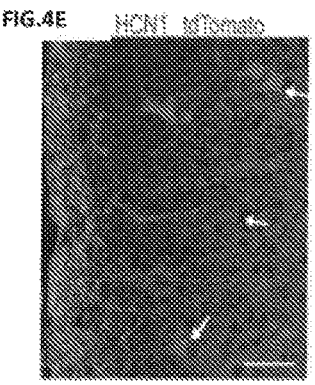 FIG. 4F  FIG. 4G 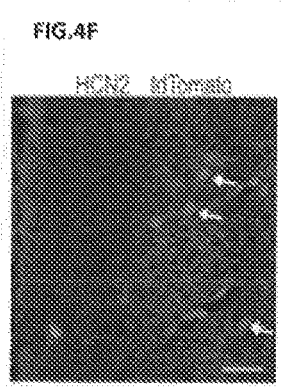
FIG. 4H 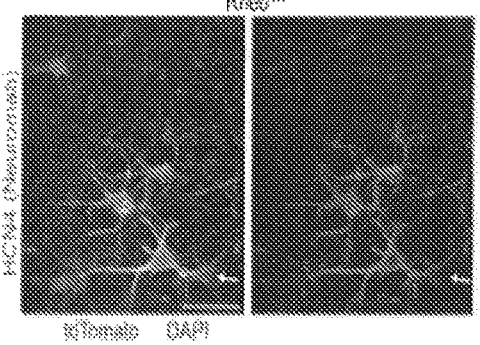 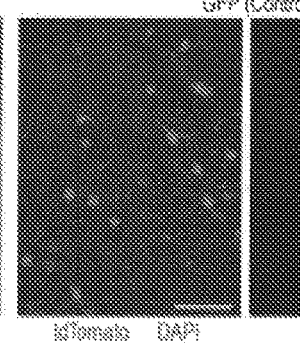 FIG. 4I 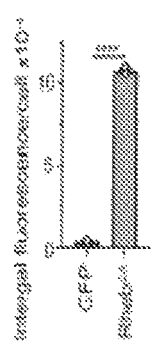

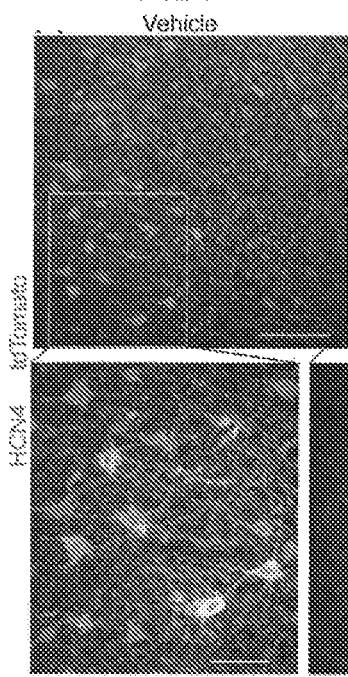
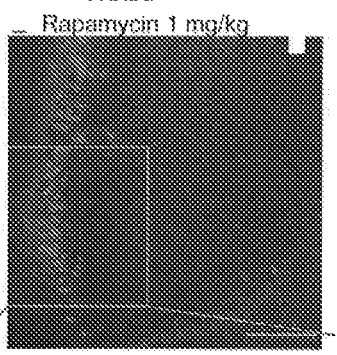
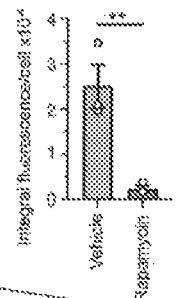
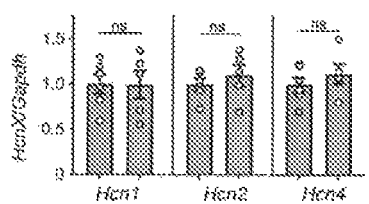
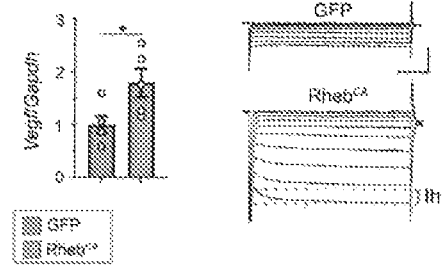
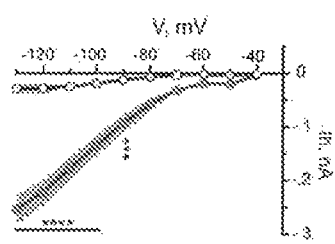
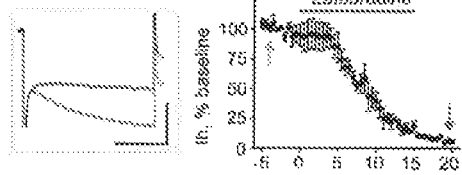
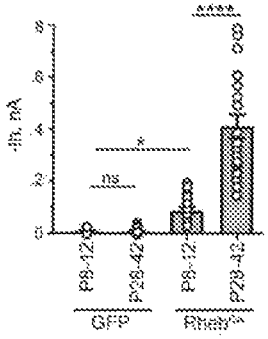

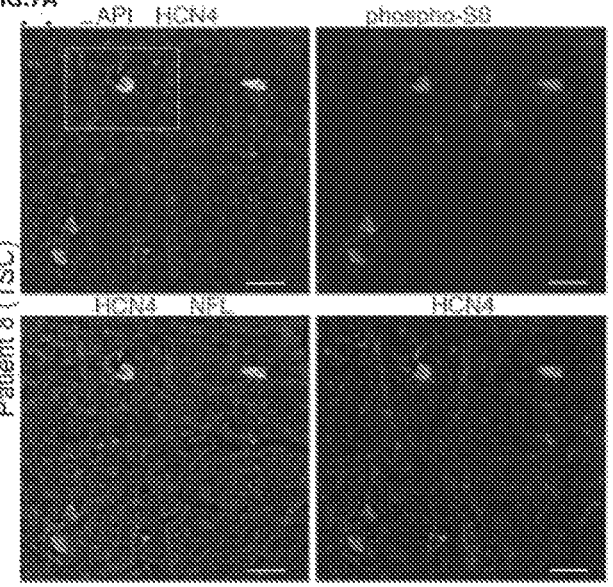
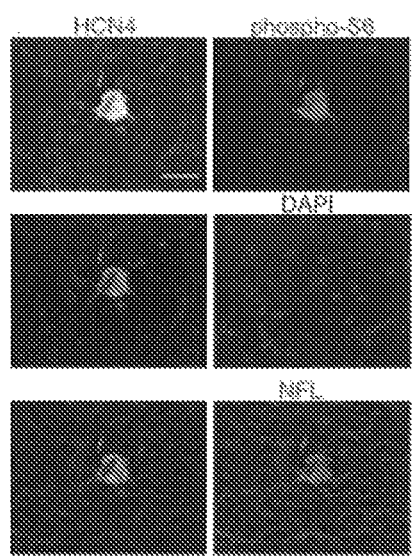
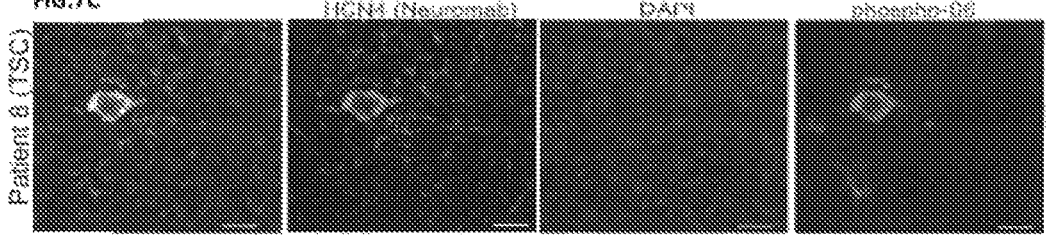
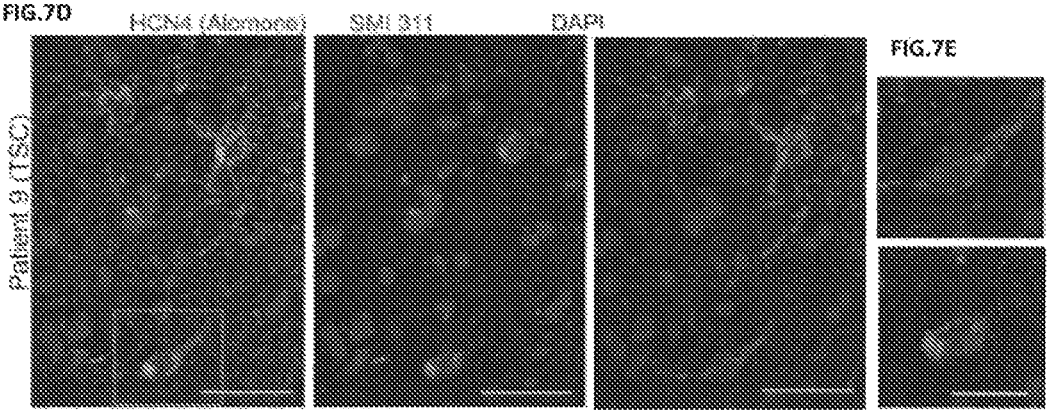

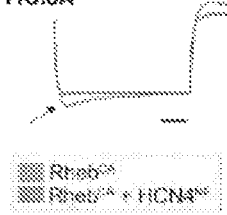
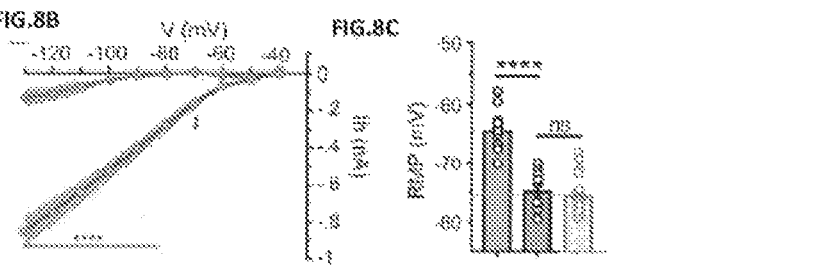
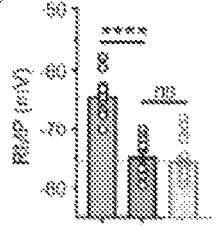
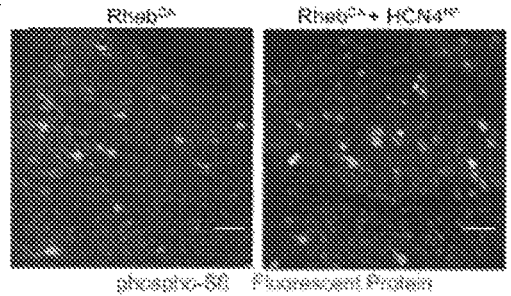
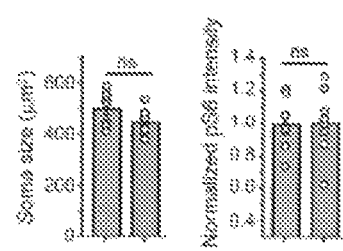
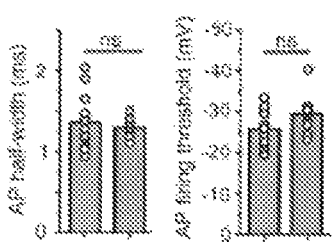
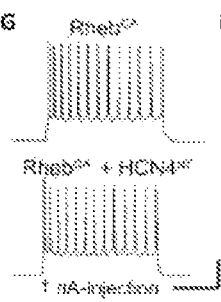
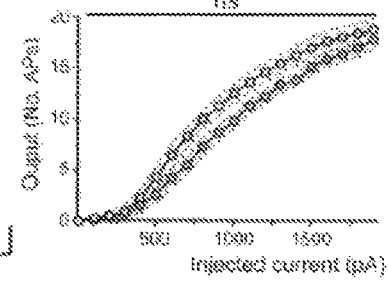
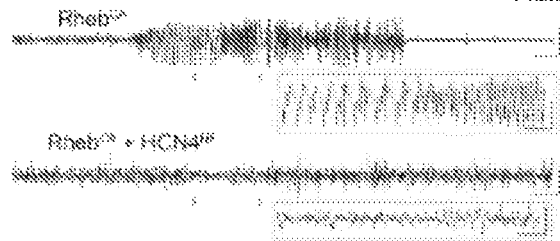
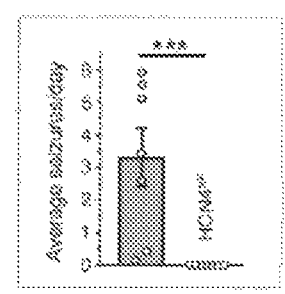

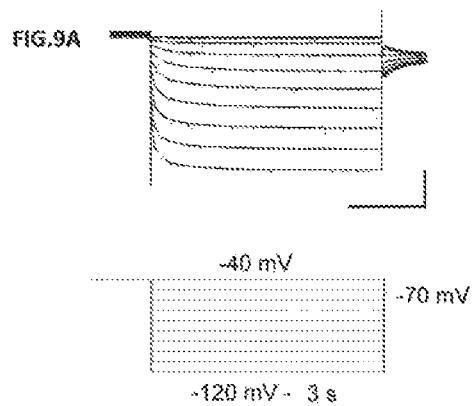
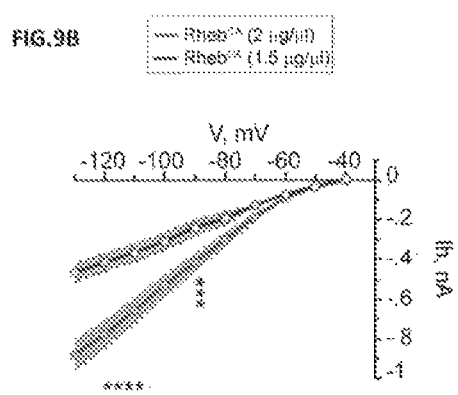

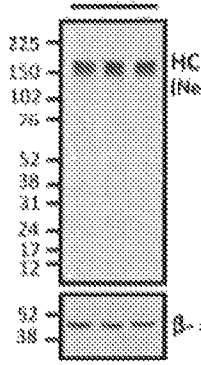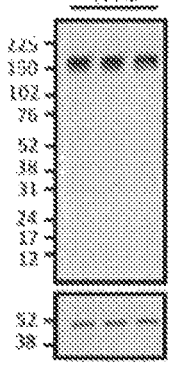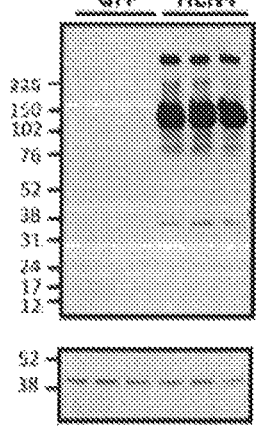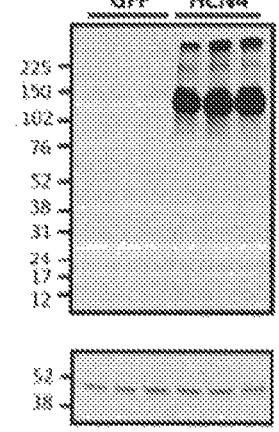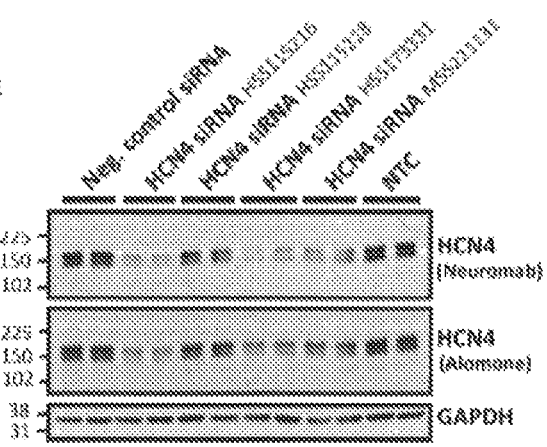

HCN4 + tdTomato plasmids

FIG. 14A
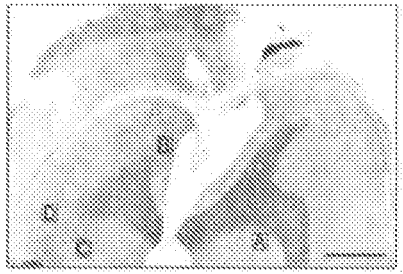
FIG. 14B
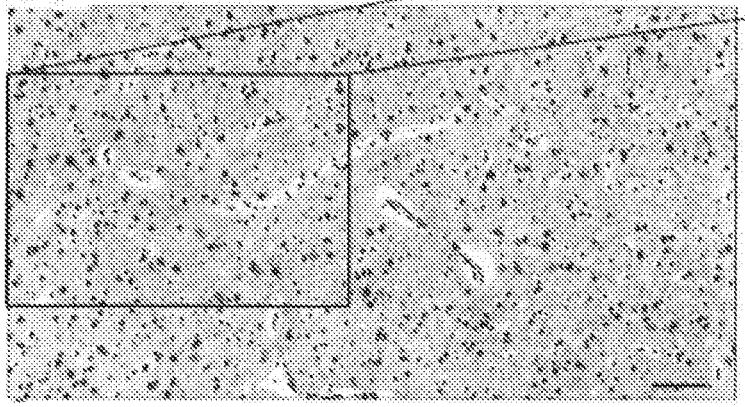
FIG. 14C
FIG. 14D
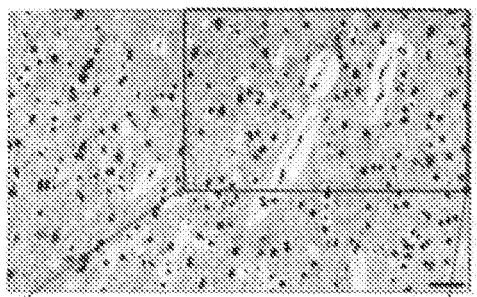
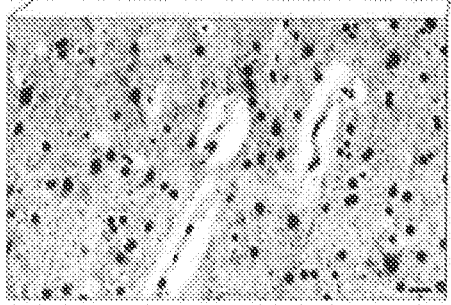
FIG. 14E
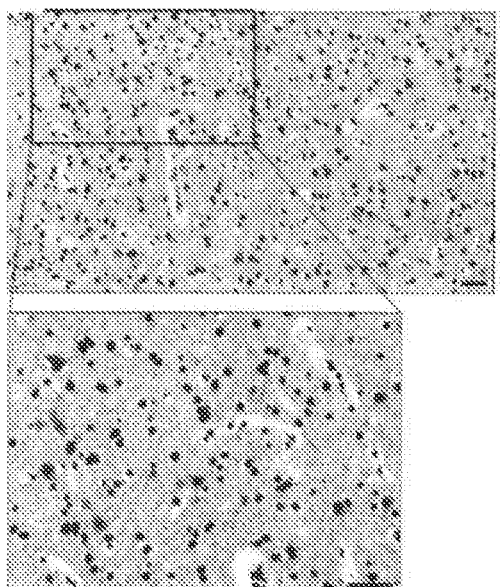

FIG. 15A HCN4 Hematoxylin FIG. 15B
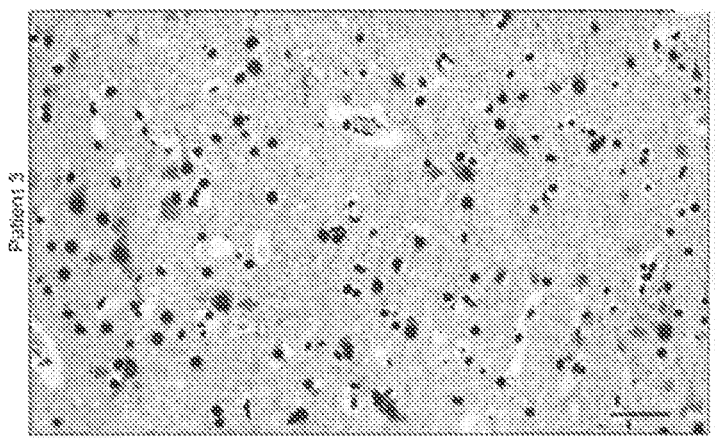
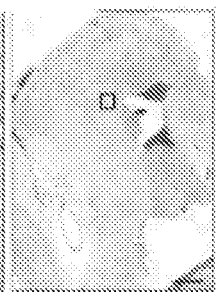
FIG. 15C
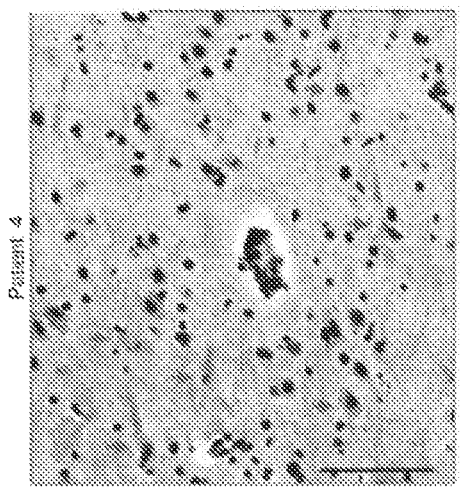
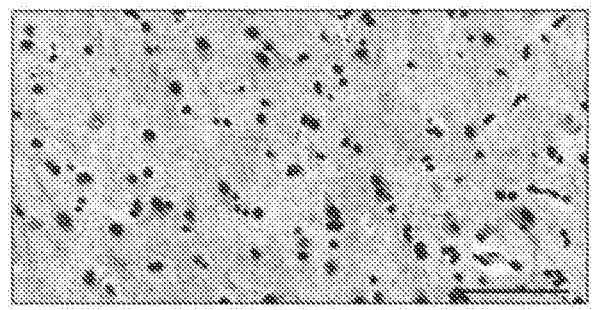
FIG. 15D
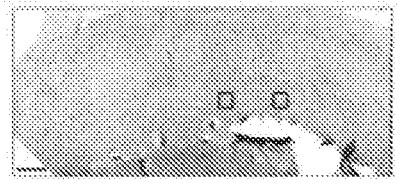
FIG. 15E
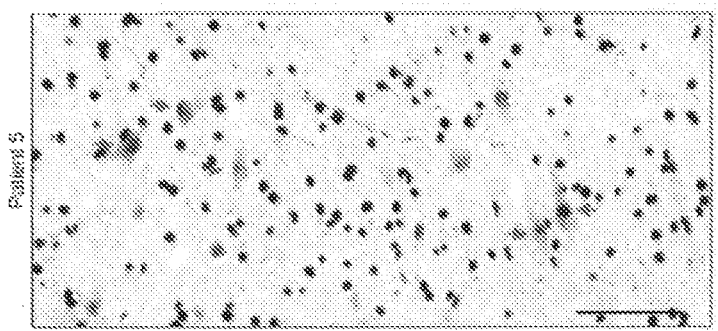

FIG. 16A                FIG. 16B                FIG. 16C
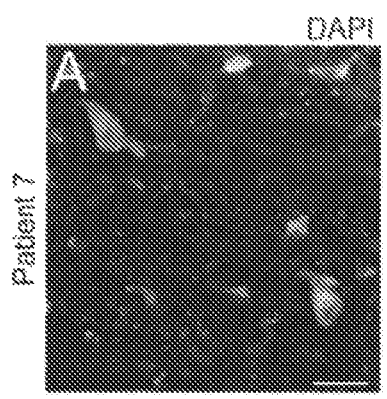 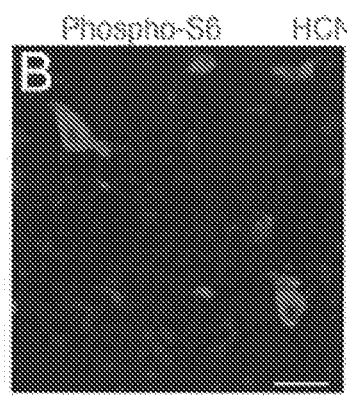 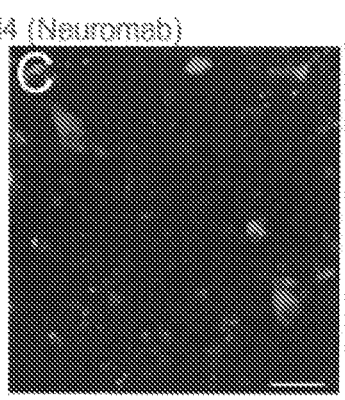
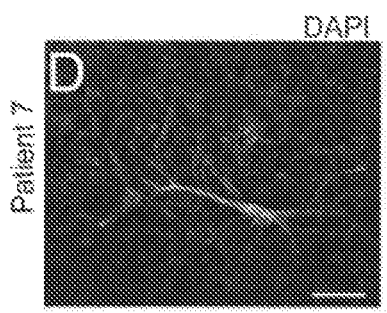 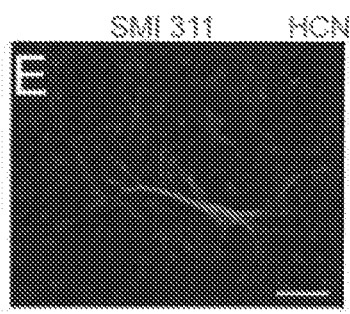 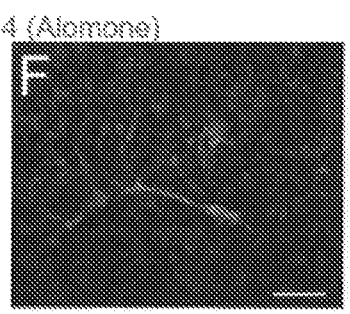
FIG. 16D                FIG. 16E                FIG. 16F

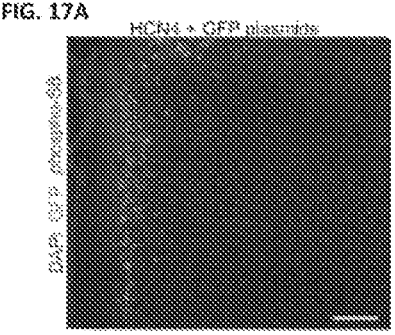
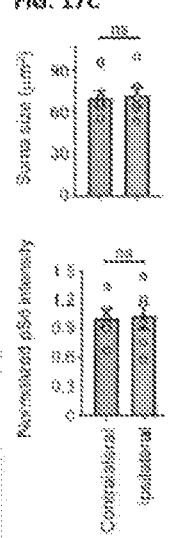
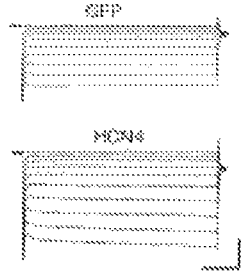
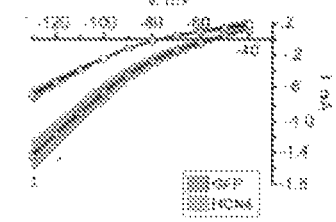
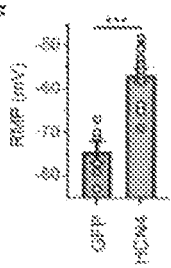
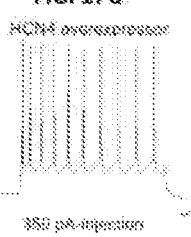
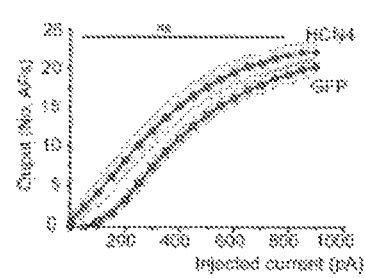
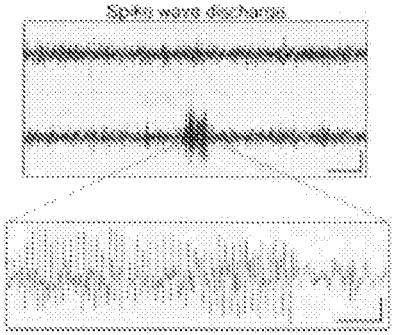
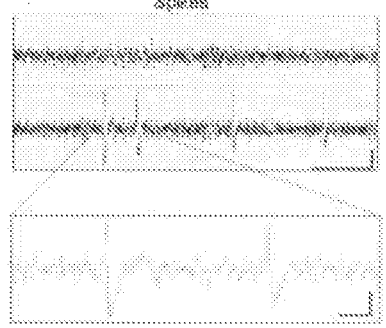

SEQUENCE LISTING

```
<160> NUMBER OF SEQ ID NOS: 11

<210> SEQ ID NO 1
<211> LENGTH: 1186
<212> TYPE: PRT
<213> ORGANISM: Homo sapiens

<400> SEQUENCE: 1

Met Asp Lys Leu Pro Pro Ser Met Arg Lys Arg Leu Tyr Ser Leu Pro
1               5                   10                  15

Gln Gln Val Gly Ala Lys Ala Trp Ile Met Asp Glu Glu Glu Asp Gly
            20                  25                  30

Glu Glu Glu Gly Ala Gly Gly Arg Gln Asp Pro Ser Arg Arg Ser Ile
        35                  40                  45

Arg Leu Arg Pro Leu Pro Ser Pro Ser Pro Ser Val Ala Ala Gly Cys
    50                  55                  60

Ser Glu Ser Arg Gly Ala Ala Leu Gly Ala Thr Glu Ser Glu Gly Pro
```

```
            65                  70                  75                  80
Gly Arg Ser Ala Gly Lys Ser Ser Thr Asn Gly Asp Cys Arg Arg Phe
                    85                  90                  95
Arg Gly Ser Leu Ala Ser Leu Gly Ser Arg Gly Gly Ser Gly Gly
            100                 105                 110
Ala Gly Gly Ser Ser Leu Gly His Leu His Asp Ser Ala Glu Glu
            115                 120                 125
Arg Arg Leu Ile Ala Ala Glu Gly Asp Ala Ser Pro Gly Glu Asp Arg
    130                 135                 140
Thr Pro Pro Gly Leu Ala Thr Glu Pro Glu Arg Pro Ala Thr Ala Ala
145                 150                 155                 160
Gln Pro Ala Ala Ser Pro Pro Gln Gln Pro Pro Gln Pro Ala Ser
                165                 170                 175
Ala Ser Cys Glu Gln Pro Ser Ala Asp Thr Ala Ile Lys Val Glu Gly
            180                 185                 190
Gly Ala Ala Ala Ile Asp His Ile Leu Pro Glu Ala Glu Val Arg Leu
            195                 200                 205
Gly Gln Ser Gly Phe Met Gln Arg Gln Phe Gly Ala Met Leu Gln Pro
    210                 215                 220
Gly Val Asn Lys Phe Ser Leu Arg Met Phe Gly Ser Gln Lys Ala Val
225                 230                 235                 240
Glu Arg Glu Gln Glu Arg Val Lys Ser Ala Gly Phe Trp Ile Ile His
                245                 250                 255
Pro Tyr Ser Asp Phe Arg Phe Tyr Trp Asp Leu Thr Met Leu Leu Leu
            260                 265                 270
Met Val Gly Asn Leu Ile Ile Ile Pro Val Gly Ile Thr Phe Phe Lys
            275                 280                 285
Asp Glu Asn Thr Thr Pro Trp Ile Val Phe Asn Val Val Ser Asp Thr
    290                 295                 300
Phe Phe Leu Ile Asp Leu Val Leu Asn Phe Arg Thr Gly Ile Val Val
305                 310                 315                 320
Glu Asp Asn Thr Glu Ile Ile Leu Asp Pro Gln Arg Ile Lys Met Lys
                325                 330                 335
Tyr Leu Lys Ser Trp Phe Val Val Asp Phe Ile Ser Ser Ile Pro Val
            340                 345                 350
Glu Tyr Ile Phe Leu Ile Val Glu Thr Arg Ile Asp Ser Glu Val Tyr
            355                 360                 365
Lys Thr Ala Arg Ala Val Arg Ile Val Arg Phe Thr Lys Ile Leu Ser
    370                 375                 380
Leu Leu Arg Leu Leu Arg Leu Ser Arg Leu Ile Arg Tyr Ile His Gln
385                 390                 395                 400
Trp Glu Glu Ile Phe His Met Thr Tyr Asp Leu Ala Ser Ala Val Val
                405                 410                 415
Arg Ile Val Asn Leu Ile Gly Met Met Leu Leu Leu Cys His Trp Asp
            420                 425                 430
Gly Cys Leu Gln Phe Leu Val Pro Met Leu Gln Asp Phe Pro His Asp
            435                 440                 445
Cys Trp Val Ser Ile Asn Gly Met Val Asn Asn Ser Trp Gly Lys Gln
            450                 455                 460
Tyr Ser Tyr Ala Leu Phe Lys Ala Met Ser His Met Leu Cys Ile Gly
465                 470                 475                 480
Tyr Gly Arg Gln Ala Pro Val Gly Met Ser Asp Val Trp Leu Thr Met
                485                 490                 495
```

-continued

Leu Ser Met Ile Val Gly Ala Thr Cys Tyr Ala Met Phe Ile Gly His
            500                 505                 510
Ala Thr Ala Leu Ile Gln Ser Leu Asp Ser Ser Arg Gln Tyr Gln
        515                 520                 525
Glu Lys Tyr Lys Gln Val Glu Gln Tyr Met Ser Phe His Lys Leu Pro
            530                 535                 540
Pro Asp Thr Arg Gln Arg Ile His Asp Tyr Tyr Glu His Arg Tyr Gln
545                 550                 555                 560
Gly Lys Met Phe Asp Glu Ser Ile Leu Gly Leu Ser Glu Pro
            565                 570                 575
Leu Arg Glu Glu Ile Ile Asn Phe Asn Cys Arg Lys Leu Val Ala Ser
            580                 585                 590
Met Pro Leu Phe Ala Asn Ala Asp Pro Asn Phe Val Thr Ser Met Leu
        595                 600                 605
Thr Lys Leu Arg Phe Glu Val Phe Gln Pro Gly Asp Tyr Ile Ile Arg
        610                 615                 620
Glu Gly Thr Ile Gly Lys Lys Met Tyr Phe Ile Gln His Gly Val Val
625                 630                 635                 640
Ser Val Leu Thr Lys Gly Asn Lys Glu Thr Arg Leu Ala Asp Gly Ser
            645                 650                 655
Tyr Phe Gly Glu Ile Cys Leu Leu Thr Arg Gly Arg Arg Thr Ala Ser
            660                 665                 670
Val Arg Ala Asp Thr Tyr Cys Arg Leu Tyr Ser Leu Ser Val Asp Asn
        675                 680                 685
Phe Asn Glu Val Leu Glu Glu Tyr Pro Met Met Arg Lys Lys Asn Ser
        690                 695                 700
Ile Leu Leu His Lys Val Gln His Asp Leu Asn Ser Gly Val Phe Asn
705                 710                 715                 720
Tyr Gln Glu Asn Glu Ile Ile Gln Gln Ile Val Arg His Asp Arg Glu
            725                 730                 735
Met Ala His Cys Ala His Arg Val Gln Ala Ala Ala Ser Ala Thr Pro
            740                 745                 750
Thr Pro Thr Pro Val Ile Trp Thr Pro Leu Ile Gln Ala Pro Leu Gln
        755                 760                 765
Ala Ala Ala Ala Thr Thr Ser Val Ala Ile Ala Leu Thr His His Pro
        770                 775                 780
Arg Leu Pro Ala Ala Ile Phe Arg Pro Pro Gly Pro Gly Leu Gly
785                 790                 795                 800
Asn Leu Gly Ala Gly Gln Thr Pro Arg His Pro Arg Arg Leu Gln Ser
            805                 810                 815
Leu Ile Pro Ser Ala Leu Gly Ser Ala Ser Pro Ala Ser Ser Pro Ser
            820                 825                 830
Gln Val Asp Thr Pro Ser Ser Ser Phe His Ile Gln Gln Leu Ala
        835                 840                 845
Gly Phe Ser Ala Pro Pro Gly Leu Ser Pro Leu Leu Pro Ser Ser Ser
        850                 855                 860
Ser Ser Pro Pro Pro Gly Ala Cys Gly Ser Pro Pro Ala Pro Thr Pro
865                 870                 875                 880
Ser Thr Ser Thr Ala Ala Ala Ala Ser Thr Thr Gly Phe Gly His Phe
            885                 890                 895
His Lys Ala Leu Gly Gly Ser Leu Ser Ser Ser Asp Ser Pro Leu Leu
            900                 905                 910

Thr Pro Leu Gln Pro Gly Ala Arg Ser Pro Gln Ala Gln Pro Pro
        915                 920                 925

Pro Pro Leu Pro Gly Ala Arg Gly Gly Leu Gly Leu Leu Glu His Phe
    930                 935                 940

Leu Pro Pro Pro Ser Ser Arg Ser Pro Ser Ser Ser Pro Gly Gln
945                 950                 955                 960

Leu Gly Gln Pro Pro Gly Glu Leu Ser Leu Gly Leu Ala Ala Gly Pro
            965                 970                 975

Ser Ser Thr Pro Glu Thr Pro Pro Arg Pro Glu Arg Pro Ser Phe Met
            980                 985                 990

Ala Gly Ala Ser Gly Gly Ala Ser Pro Val Ala Phe Thr Pro Arg Gly
            995                 1000                1005

Gly Leu Ser Pro Pro Gly His Ser Pro Gly Pro Pro Arg Thr Phe
    1010                1015                1020

Pro Ser Ala Pro Pro Arg Ala Ser Gly Ser His Gly Ser Leu Leu
    1025                1030                1035

Leu Pro Pro Ala Ser Ser Pro Pro Pro Gln Val Pro Gln Arg
    1040                1045                1050

Arg Gly Thr Pro Pro Leu Thr Pro Gly Arg Leu Thr Gln Asp Leu
    1055                1060                1065

Lys Leu Ile Ser Ala Ser Gln Pro Ala Leu Pro Gln Asp Gly Ala
    1070                1075                1080

Gln Thr Leu Arg Arg Ala Ser Pro His Ser Ser Gly Glu Ser Val
    1085                1090                1095

Ala Ala Phe Ser Leu Tyr Pro Arg Ala Gly Gly Gly Ser Gly Ser
    1100                1105                1110

Ser Gly Gly Leu Gly Pro Pro Gly Arg Pro Tyr Gly Ala Ile Pro
    1115                1120                1125

Gly Gln His Val Thr Leu Pro Arg Lys Thr Ser Gly Ser Leu
    1130                1135                1140

Pro Pro Pro Leu Ser Leu Phe Gly Ala Arg Ala Ala Ser Ser Gly
    1145                1150                1155

Gly Pro Pro Leu Thr Thr Ala Ala Pro Gln Arg Glu Pro Gly Ala
    1160                1165                1170

Arg Ser Glu Pro Val Arg Ser Lys Leu Pro Ser Asn Leu
    1175                1180                1185

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
caaattctcc ctccgcatgt t                                        21

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
tgaagaacgt gattccaact gg                                       22

```
<210> SEQ ID NO 4
<211> LENGTH: 19
<212> TYPE: DNA
<213> ORGANISM: Artificial Sequence
<220> FEATURE:
<223> OTHER INFORMATION: Primer

<400> SEQUENCE: 4
ccggcgtcaa caagttctc                                                   19

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
tgcccacggg aatgataatg a                                                21

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
ggcggacacc gctatcaaa                                                   19

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
tgccgaacat ccttagggag a                                                21

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
agccgagctc atggacgggt                                                  20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ctgtcgtggg tgcagcctgg                                                  20

<210> SEQ ID NO 10
<211> LENGTH: 17
<212> TYPE: DNA
<213> ORGANISM: Artificial Sequence
<220> FEATURE:
<223> OTHER INFORMATION: Primer
```

```
<400> SEQUENCE: 10
accaccatgg agaaggc                                                17

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
ggcatggact gtggtcatga                                             20
```

METHODS OF TREATING AND DIAGNOSING EPILEPSY

CROSS-REFERENCE TO RELATED APPLICATIONS

The present application is a 35 U.S.C. & 371 national phase application from, and claims priority to, International Application No. PCT/US2020/020994 filed Mar. 4, 2020, which claims priority under 35 U.S.C. § 119(e) to U.S. Provisional Patent Application No. 62/813,429 filed Mar. 4, 2019, all of which are incorporated herein by reference in their entireties.

STATEMENT REGARDING FEDERALLY SPONSORED RESEARCH OR DEVELOPMENT

This invention was made with government support under NS093510, NS111980 and NS093704 awarded by National Institutes of Health and under W81XH-16-1-0164 awarded by United States Army Medical Research and Material Command. The government has certain rights in the invention.

SEQUENCE LISTING

The ASCII text file named "38938641_1.txt" created on Sep. 2, 2021, comprising 12,378 bytes, is hereby incorporated by reference in its entirety.

BACKGROUND OF THE INVENTION

Disorders caused by mutations in the mTOR pathway genes lead to mTOR hyperactivity, brain malformations, and life-long epilepsy in the majority of patients. Among this group of disorders, focal conical dysplasia (FCD) and tuberous sclerosis complex (TSC) account for the largest population of children and young adults that undergo brain surgery to treat intractable epilepsy. These patients display focal cortical malformations (FCM) that generate seizure foci. Surgical resection of the seizure foci or pharmacological inhibition of mTOR signaling in the case of TSC am the only available treatments for mTOR-dependent focal epilepsy, but neither option is fully effective. Despite the identification of the molecular pathway dysregulated in TSC and FCDII, and the pathological characteristics associated with seizures, the mechanism of epileptogenesis remains unknown. In addition, the exact site and the cell types responsible for epileptogenic activity in humans remain controversial as some studies have recorded epileptic discharges both inside and outside of FCM whereas other studies have found FCM to be electrically silent. The lack of consensus on the site of seizure generation further reflects this poor understanding of the epileptogenic mechanisms, which has hampered the identification of novel therapeutic targets and effective treatment options. There is a need in the art for novel methods for diagnosing and treating epilepsy. This disclosure addresses that need.

SUMMARY OF THE INVENTION

In one aspect, the invention provides a method of treating epilepsy in a subject in need thereof, the method comprising contacting a target cell of the subject with an effective amount of an HCN4 disrupting agent.

In another aspect, the invention provides a method of diagnosing epilepsy in a subject, the method comprising administering to the subject an effective amount of an HCN4 detecting agent.

In certain embodiments, the HCN4 disrupting agent is a viral vector encoding a polynucleotide or polynucleotides that reduce or eliminate HCN4 activity.

In certain embodiments, the the HCN4 disrupting agent is selected from the group consisting of a non-functional HCN4 (HCN4$^{NF}$ acting as a dominant negative), an antisense RNA, antigomer RNA, siRNA, shRNA, and a CRISPR system.

In certain embodiments, the HCN4 disrupting agent is an adenoviral vector comprising a polynucleotide encoding HCN4$^{NF}$.

In certain embodiments, the HCN4 disrupting agent is encapsulated in LHNP nanoparticles.

In certain embodiments, the HCN4 disrupting agent is a CRISPR system.

In certain embodiments, the target cell is a focal-cortical malformation (FCM) neuron.

In certain embodiments, the HCN4 disrupting agent is locally administered to the FCM neuron.

In certain embodiments, the epilepsy comprises an mTORopathy.

In certain embodiments, the epilepsy is focal cortical dysplasia type II (FCDII) or tuberous sclerosis complex (TSC).

In certain embodiments, the epilepsy results from Cowden syndrome (PTEN mutation), brain trauma, genetic disorders due to mutations in PI3K-AKT-mTOR gene pathways or in GATOR gene pathway, and brain tumors.

In certain embodiments, the HCN4 detecting agent is selected from the group consisting of a labeled antibody that binds to HCN4 and a PET tracer that binds to HCN4.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A-II depict model of mTOR-dependent FCM-associated seizures. (FIG. 1A) Timeline of the experimental paradigm. (FIG. 1B) Diagram of Rheb$^{CA}$ effect on mTOR complex 1 (mTORC1). (FIG. 1C) Diagram of a mouse brain with superimposed image of a FCM in the medial prefrontal cortex (mPFC). Linked circles mark the approximate locations of independent pairs of recording electrodes in the ipsilateral and contralateral hemispheres. (FIG. 1D) Confocal images of GFP and tdTomato (noted fluorescent proteins) fluorescence and phospho-S6 immunostaining in coronal sections from 3 months old mice expressing GFP (control) or Rheb$^{CA}$ (+tdTomato) in the mPFC. Scale bars: 150 µm. (FIG. 1E) Bar graphs of soma size of GFP and Rheb$^{CA}$-expressing neurons, Student's t test. (FIG. 1F) B&W phospho-S6 immunostaining from images shown in FIG. 1D. Scale bar: 150 µm. (FIG. 1G) Bar graphs of phospho-S6 (pS6) immunofluorescence in GFP and Rheb$^{CA}$-expressing neurons, Student's t test. (FIG. 1H) Image of the video-EEG set-up. (FIG. 1I) Representative examples of an EEG trace and higher temporal resolution traces in the inset. Scale bars: 10 s/200 µV and 2 s/200 µV (inset). Data are mean±SEM. *: P<0.001. **: P<0.0001, ns: not significant. Exact P values can be found in Table 4.

FIGS. 2A-2J depict that silencing cytomegalic neurons in mTOR-driven FCM prevents seizure activity. (FIG. 2A) Confocal images of GFP and tdTomato fluorescence and phospho-S6 immunostaining (red) in coronal sections from 4 months old littermate mice (used in panel J) expressing $Rheb^{CA}$+GFP or +Kir2.1 (fused to tdTomato). Scale bar: 100 µm. (FIG. 2B) B&W phospho-S6 immunostaining from images shown in A. (FIG. 2C) Bar graphs of normalized phospho-S6 immunofluorescence intensity and soma size of $Rheb^{CA}$ neurons co-expressing GFP or Kir2.1. Student's t test. (FIG. 2D) Bar graphs of cell capacitance, resting membrane potential (RMP) and membrane conductance of $Rheb^{CA}$ neurons co-expressing GFP or Kir2.1. Patch clamp recordings were obtained in acute slices from P26-P42 mice, Student's t test. (FIG. 2E) Superimposed individual action potentials from $Rheb^{CA}$ neurons in both conditions. Scale bars: 2 ms/40 mV. (FIG. 2F) Bar graphs of the action potential (AP) half-width and threshold. Student's t test. (FIG. 2G) Representative depolarization and action potentials upon current injection in $Rheb^{CA}$ co-expressing GFP or Kir2.1. Scales: 200 ms/40 mV. (FIG. 2H) Injected current amplitude plotted as a function of the mean number of action potentials for generating an input-output curve in $Rheb^{CA}$ neurons. Two-way repeated measure ANOVA, followed by Sidak post-test. The grey area outlines the SEM for each curve. (FIG. 2I) Heat map of the number of seizures over a 7-day long recording period in mice containing $Rheb^{CA}$ neurons with GFP or Kir2.1. (FIG. 2J) Bar graphs of the duration and number of seizures per day in the two conditions. Student's t test (seizure frequency) and Mann Whitney U test (seizure duration). Data are mean±SEM. *: P<0.05, : P<0.01, *: P<0.001, ****: P<0,0001, as: not significant. Exact P values can be found in Table 4.

FIGS. 3A-3M depict that abnormal HCN currents in FCM neurons are depolarizing and confer cAMP-dependent firing. (FIG. 3A and FIG. 3B) Bar graphs of the RMP and conductance of control (GFP) and $Rheb^{CA}$ neurons recorded in littermate P26-P42 mice. Student's t test. (FIG. 3C) Representative depolarization and action potentials upon current injection in $Rheb^{CA}$ or control (GFP) neurons. Scales: 100 ms/40 mV. (FIG. 3D) Injected current amplitude plotted as a function of the mean number of action potentials for generating an input-output curve in $Rheb^{CA}$ neurons. Two-way repeated measure ANOVA, followed by Sidak post-test. The grey area outlines the SEM for each curve. (FIG. 3E) Representative voltage traces in response to a −500 pA current step in neurons expressing GFP or $Rheb^{CA}$. Neurons were recorded in current-clamp at their RMP and voltage traces were superimposed post-recording. The arrow points to a hyperpolarization-induced voltage sag. Scales: 100 ms/10 mV. (FIG. 3F) Voltage traces in response to a −500 pA current step from GFP-expressing neurons, $Rheb^{CA}$-expressing neurons, and $Rheb^{CA}$ expressing neurons in the presence of zatebradine (40 µM, red). Voltage responses were rescaled and superimposed post-recording. Scale: 100 ms. (FIG. 3G) Representative current traces in cortical neurons expressing GFP (control), $Rheb^{CA}$, or $Rheb^{CA}$ with zatebradine (FIG. 3D), Protocol: conditioning step to −40 mV followed by 10 mV hyperpolarizing steps from −130 to −40 mV. Scale bars: 200 ms/1 nA. The dotted lines illustrate where the difference in current amplitude (ΔI) was measured within each voltage step to generate current-voltage (ΔI-V) curves in FIG. 3H. (FIG. 3H) Current amplitude (I measured at the end of the trace) versus the voltage in each condition. The grey area indicates the SEM for each curve. Two-way repeated measures ANOVA followed by Tukey post-test. (FIG. 3I) Bar graphs of the RMP for each condition. Control from panel A was added for comparison, Student's t test. (FIG. 3J) ΔI-V curves. At −90 mV, ΔI corresponds to Ih. Two-way repeated measures ANOVA followed by Tukey post-test, Statistics is for $Rheb^{CA}$ vs $Rheb^{CA}$+zatebradine. (FIG. 3K) Scatter plot of Ih (measured at −90 mV step) against the RMP. Two-tailed Pearson r with correlation coefficients. (FIG. 3L and FIG. 3M) Increasing intracellular cAMP via forskolin bath-application significantly depolarized $Rheb^{CA}$ neurons but not control neurons, and it induced (triggered) repetitive (regenerative) firing in 4/9 $Rheb^{CA}$ neurons. Scale bars: 5 min/30 mV. Paired Student's t test. Data are mean±SEM. **:P<0.0001, *: P<0001, *:P<0.05, and ns: not significant. Exact P values can be found in Table 4.

FIGS. 4A-4I depict that FCM neurons display abnormal mTOR-dependent HCN4 expression. (FIG. 4A-FIG. 4D) Immunostaining for HCN1 (FIG. 4A). HCN2 (FIG. 4B) and HCN4 (FIG. 4C) in coronal sections containing $Rheb^{CA}$ neurons co-expressing tdTomato. HCN4 staining was performed using antibodies from Neuromab and Alamone. The bottom images display HCN staining in B&W. Scale bars: 200 µm. (FIG. 4E and FIG. 4F) Higher magnification images of HCN1 (FIG. 4E) and HCN2 (FIG. 4F) immunostaining and tdTomato from images in FIG. 4A and FIG. 4B. Scale bars: 60 µm. (FIG. 4G) Higher magnification images of HCN4, DAPI, and tdTomato. Scale bar: 60 µm, (FIG. 4H) Images of HCN4 immunostaining, tdTomato fluorescence and DAPI in GFP electroporated mice. Scale bar: 60 µm. (FIG. 4I) Bar graph of integral fluorescence per cell in mice electroporated at E15 with $Rheb^{CA}$ or GFP. Data are mean±SEM. Student t-test. P<0.0001.

FIGS. 5A-5H depict that HCN4 expression is mTOR-dependent and precedes seizure onset. (FIG. 5A and FIG. 5B) HCN4 immunostaining (Neuromab) and tdTomato fluorescence in $Rheb^{CA}$ mice treated with vehicle (FIG. 5A) or rapamycin (FIG. 5B) and higher magnification images (from different number of optical sections from C). Scale bars: 140 and 60 µm, respectively. (FIG. 5C) Integral fluorescence in cells expressing $Rheb^{CA}$ from mice treated with vehicle or rapamycin. Unpaired t-test. (FIG. 5D) normalized qRT-PCR values for Hcn1, 2, and 4 as well as Vegf divided by Gapdh from microdissected cortices from mice electroporated with GFP or $Rheb^{CA}$, (FIG. 5E and FIG. 5F) Representative current traces in P8-P12 cortical neurons expressing GFP (control) or $Rheb^{CA}$. Scale bars: 100 ns/500 pA. The dotted lines illustrate where the h current amplitude (h) was measured within each voltage step to generate current-voltage (Ih-V) curves (FIG. 5F). Two-way repeated measures ANOVA followed by Tukey post-test. (FIG. 5G) Plot of the zatebradine block of Ih (measured at −90 mV) over time in a $Rheb^{CA}$ neuron. Left inset: traces of Zatebradine block at −90 mV in $Rheb^{CA}$ neurons. Scale bars: 200 ms/100 pA. (FIG. 5H) Bar graphs of −Ih at the different ages under control and $Rheb^{CA}$ conditions. One way ANOVA.

Data are mean±SEM. **:P<0.0001, *:P<0.01, *:P<0.05, and as: not significant. Exact P values can be found in Table 4.

Figure 6A:
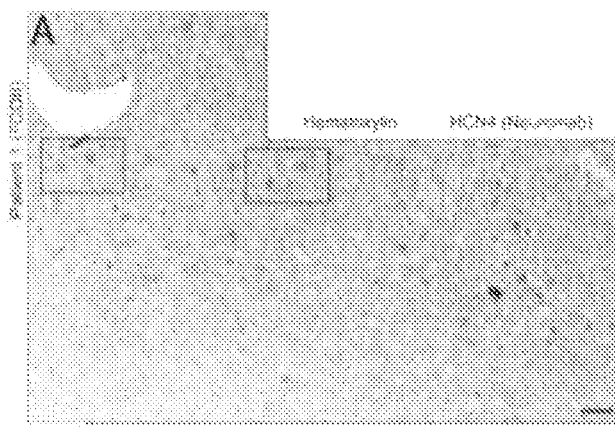
Figure 6B:
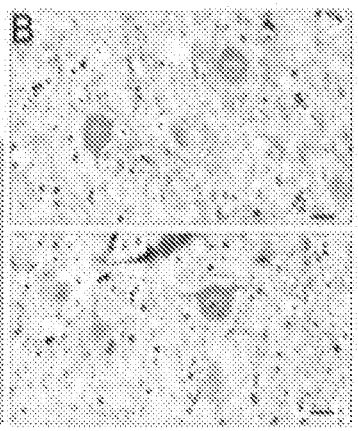
Figure 6C:
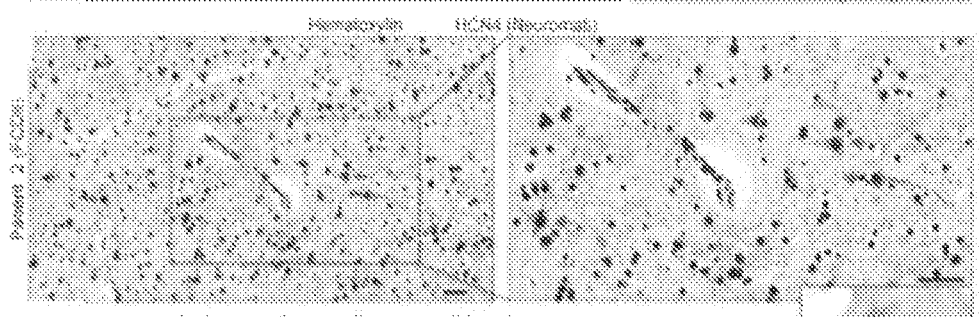
Figure 6D:
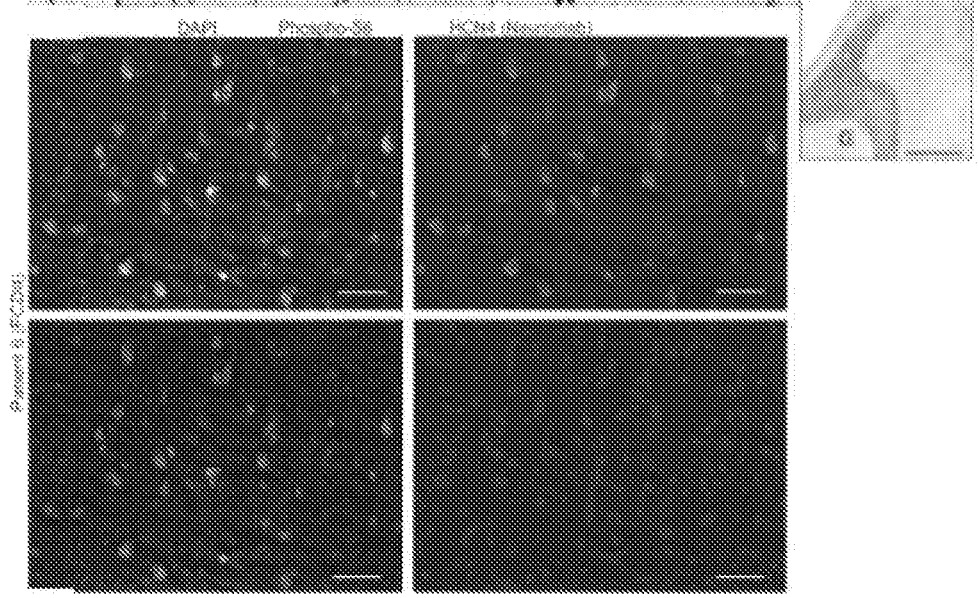
Figure 6E:
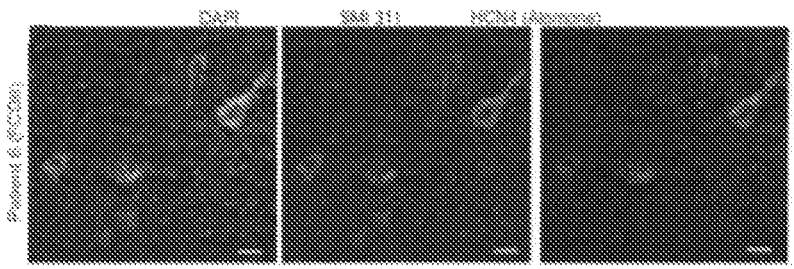

FIGS. 6A-6E depict that ectopic HCN4 expression in diseased neurons in human FCDII cortices. (FIG. 6A and FIG. 6B) Staining for HCN4 in patient 1 with FCDII at low (FIG. 6A) and high magnifications (FIG. 6B), Images in FIG. 6B was approximately from the squares in A Scale bars: 250 µm (FIG. 6A) and 30 µm (FIG. 6B). (FIG. 6C) Staining for HCN4 in patient 2 with FCDII at low and high magnifications. Scale bars: 250 µm (FIG. 6A) and 30 µm (FIG. 6B). (FIG. 6D and FIG. 6E) Immunostaining for HCN4 and phospho-S6 or SMI311 in FCDII tissue from patient 6 co-stained with DAPI. Scale bars: 70 μm. The arrows point to HCN4-positive cells, Inset represents a lower magnification view, Scale bar: 2600 μm. (FIG. 6D and FIG. 6E) Immunostaining for HCN4 and phospho-S6 or SMI-311 in FCDII tissue from patient 6 co-stained with DAP. Scale bars: 70 μm (FIG. 6D), 30 μm (FIG. 6E).

FIGS. 7A-7E depict that ectopic HCN4 expression in diseased neurons in human TSC cortices. (FIG. 7A and FIG. 7 C) Immunostaining for HCN4 and phospho-S6 TSC tissue from patient 8 co-stained with DAPI. Scale bars: 70 μm (FIG. 7A) and 40 μm (FIG. 7C). (FIG. 7B) Higher magnification of the cell shown in the white square in A. Scale bar: 35 μm. (FIG. 7D) Immunostaining for HCN4 and SMI 311 in TSC tissue from patient 9 co-stained with DAPI. Scale bar: 40 μm, (FIG. 7E) Higher magnification of the cell shown in the white square in D. Scale bar: 20 μm FIGS. 8A-8J depict that blocking HCN4 channel activity in FCM neurons prevents epilepsy. (FIG. 8A and FIG. 8B) Representative voltage-traces of $Rheb^{CA}$ neurons with and without nonfunctional HCN4 ($HCN4^{NF}$) channels expression. Neurons were recorded in acute slices from P21-P35 littermate mice electroporated with $Rheb^{CA}$+GFP or $Rheb^{CA}$+$HCN4^{NF}$ (+tdTomato). (FIG. 8B) Ih-V curve for each condition. Two-way repeated measure ANOVA followed by Sidak post-test. (FIG. 8C) Bar graphs of RMP, The control from FIG. 2A is added for comparison. Patch clamp recordings were obtained in acute slices from P21-P35 mice. Student's t test. (FIG. 8D) Confocal images of GFP and tdTomato fluorescence and phospho-S6 immunostaining in coronal sections from 4 months old mice expressing $Rheb^{CA}$+GFP or +$HCN4^{NF}$ (+tdTomato). Scale bars: 80 μm. (FIG. 8E) Bar graphs of soma size and normalized (to GFP control cells) phospho-S6 immunofluorescence for neurons expressing $Rheb^{CA}$+GFP or $Rheb^{CA}$+$HCN4^{NF}$. Student's t test. (FIG. 8F) Bar graphs of the action potential (AP) threshold and half-width. Student's t test. (FIG. 8G) Representative depolarization and action potentials upon current injection in $Rheb^{CA}$ neurons with and without $HCN4^{NF}$. Scales: 200 ms/40 mV. (FIG. 8H) Input-output curves in $Rheb^{CA}$ neurons with and without $HCN4^{NF}$. Two-way repeated measure ANOVA followed by Sidak post-test. The grey area indicates the SEM for each curve. (FIG. 8I) Representative EEG traces in $Rheb^{CA}$ mice with and without $HCN4^{NF}$<(FIG. 8J) Bar graphs of the number of seizures per day. Mann Whitney U test. Data are mean±SEM. *: $P<0.05$, : $P<0.01$, *: $P<0.001$, ****: $P<0.0001$, ns: not significant. Exact P values can be found in Table 4.

FIGS. 9A-9B depict that the concentration of $Rheb^{CA}$ influences h current amplitudes. (FIG. 9A) 3 s-long voltage pulse to fully activate HCN currents in $Rheb^{CA}$ neurons. (FIG. 9B) Current-voltage (Ih-V) curve obtained in P35-P40 neurons containing $Rheb^{CA}$ at 1.5 μg/μl or at 2 μg/μl (same as in FIG. 3E). Two-way repeated measures ANOVA followed by Sidak post-test, ** $P<0.0001$ and *:$P<0.001$. n=8 and 20 neurons for $Rheb^{CA}$ 1.5 and 2.0 μg/μl, respectively. The grey areas illustrate the SEM for each curve. The exact statistical parameters are listed in Table 4.

FIGS. 10A-10E depict validation of HCN4 antibody specificity in IMR-32 (human neuroblastoma) cell line. (FIG. 10A-FIG. 10E) Western blots of HCN4 from lysates from non-transfected cells (FIG. 10A and FIG. 10B), lysates from cells following HCN4 overexpression (FIG. 10C and FIG. 10D), and lysates from cells following HCN4 knockdown (Invitrogen Stealth RNAi siRNAs) (FIG. 10E). Blots were probed with either a mouse HCN4 antibody (1:1000, Neuromab #75-150) (FIG. 10A, FIG. 10C. FIG. 10E) or a rabbit HCN4 antibody (1:500-1:1000, Alomone #APC-052) (FIG. 10B. FIG. 10D, FIG. 10E). β-actin (1:2000, Cell Signaling #4970) and GAPDH (1:5000, Cell Signaling #5174) were used as loading controls. Experiments were run in triplicates (FIG. 10A-FIG. 10D) and duplicates (FIG. 10E), NTC, non-transfected cells.

Figure 11A:
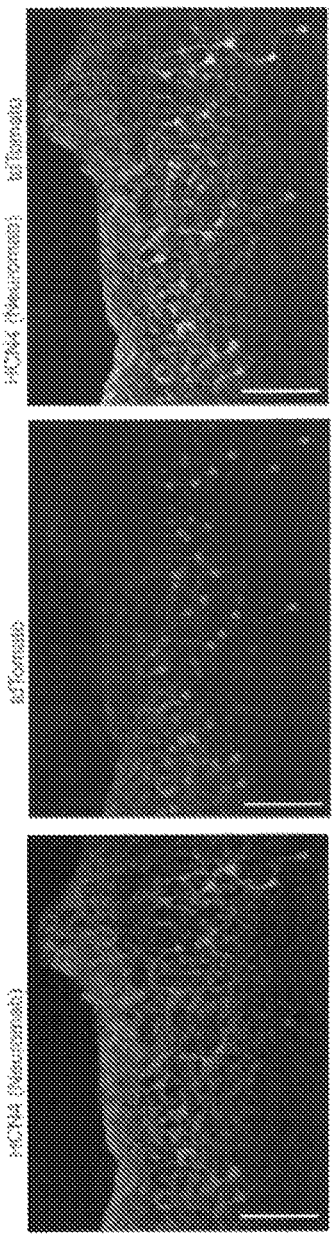
Figure 11B:
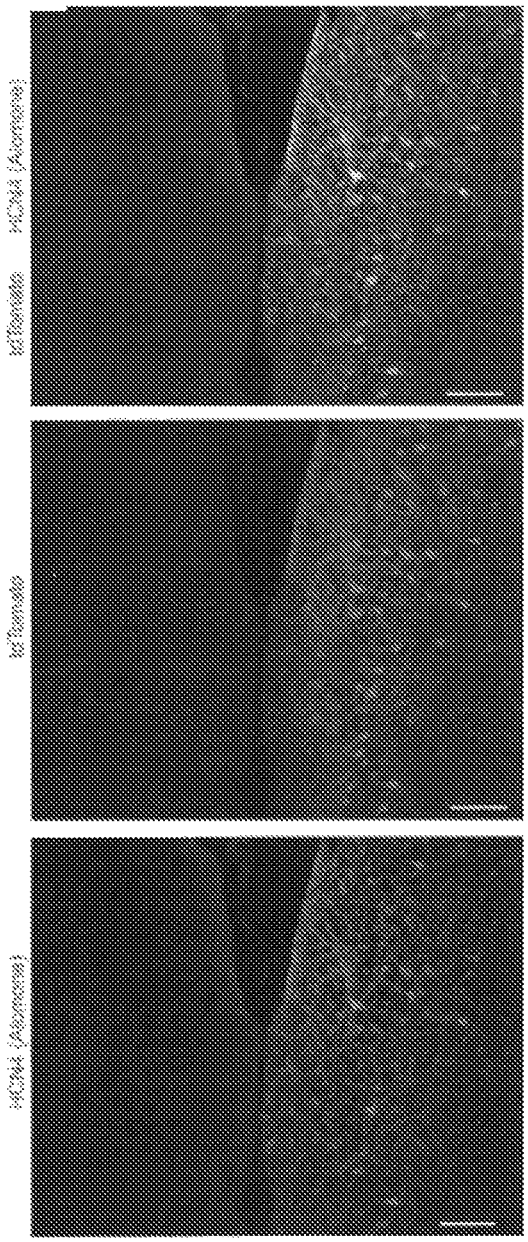
Figure 12A:
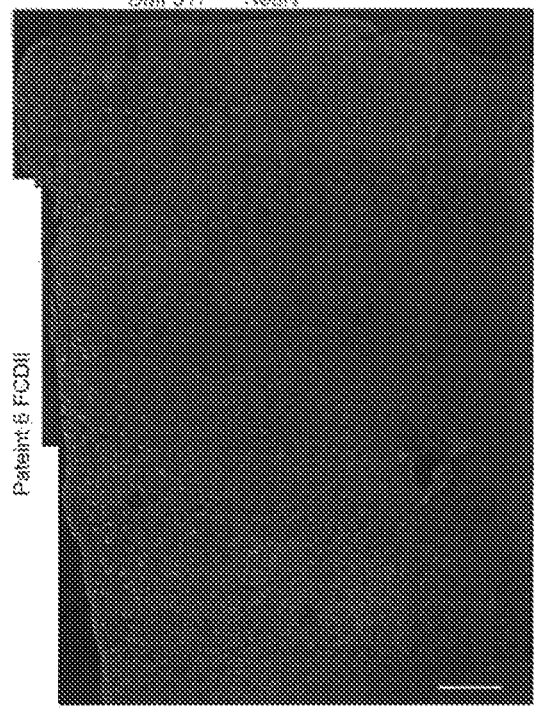
Figure 12D:
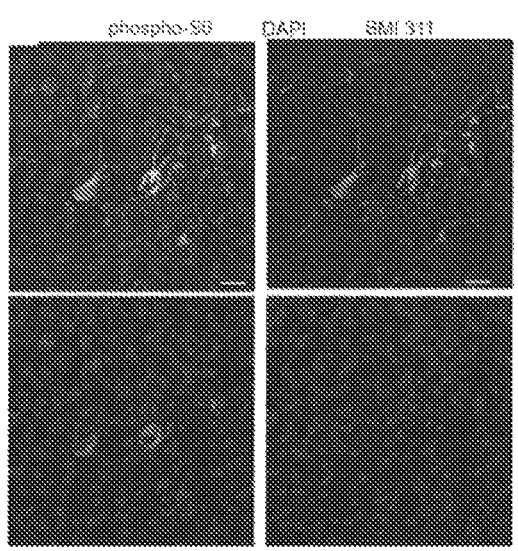
Figure 12B:
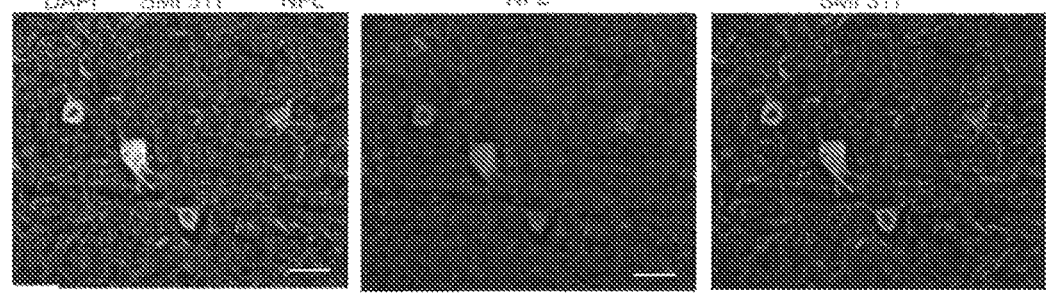
Figure 12C:
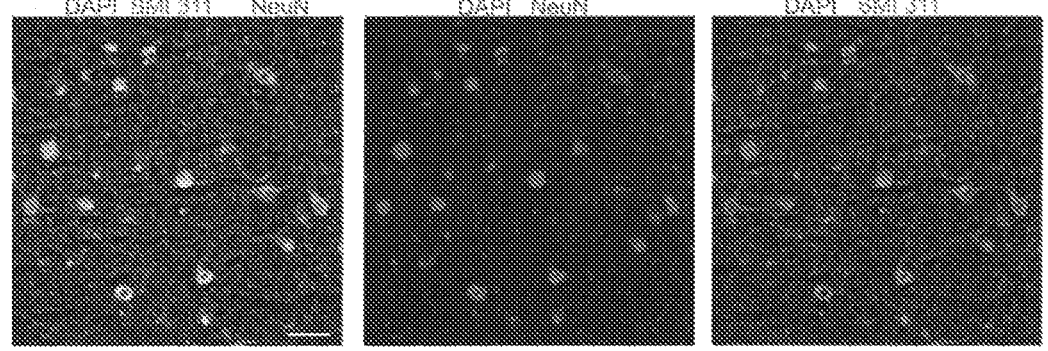

FIGS. 11A-11B depict that HCN4 antibodies detect HCN4 overexpression. (FIG. 11A and FIG. 11B) HCN4 immunostaining with Neuromab (FIG. 11A) and Alomone (FIG. 11B) antibody and tdTomato fluorescence in coronal sections from 2 months old mice containing cortical neurons electroporated with pCAG-tdTomato and pCAG-HCN4 at E15. Scale bars: 70 μm.

Figure 13:
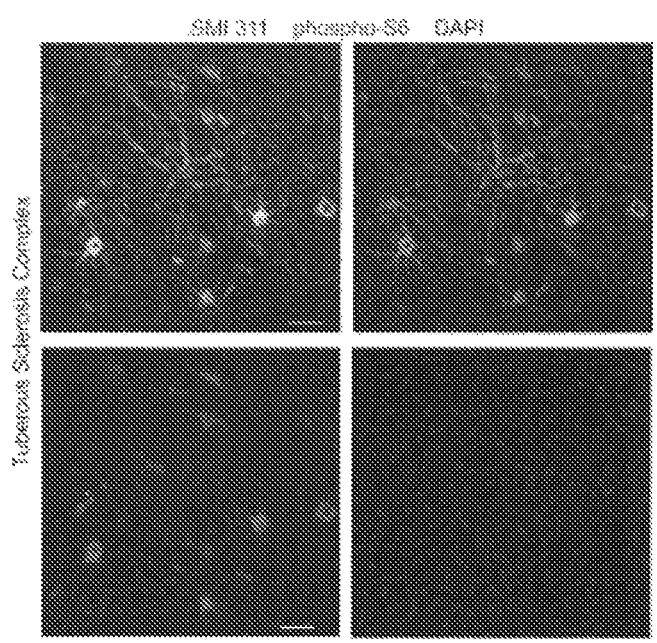

FIGS. 12A-12D depict identification of cytomegalic neurons in FCDII. (FIG. 12A) A confocal micrograph montage of cortical tissue stained with SMI 311 and NeuN from a patient with FCDII (patient 2). Scale bar: 630 μm. (FIG. 12B and FIG. 12C) Immunostaining for SMI311 and either NeuN (FIG. 12B) or NFL (FIG. 12C) in FCDII tissue (patient 2). DAPI is a nuclear stain. Scale bars: 150 μm (NeuN) and 40 μm (NFL). (FIG. 12D) immunostaining for SMI 311 and phospho-S6 in FCDII tissue co-stained with DAPI from patient 3. Scale bar: 30 μm FIG. 13 depict identification of cytomegalic neurons in TSC. Immunostaining for SMI 311 and phospho-S6 in TSC tissue co-stained with DAPI. Scale bar: 70 μm.

FIGS. 14A-14E depict identification of cytomegalic neurons in patient 2 with FCDII. (FIG. 14A) Low magnification of the FCDII tissue from patient 2. The rectangles represent the approximate regions of interest shown at higher magnification in FIG. 14 B-FIG. 14E. (FIG. 14B-FIG. 14E) Immunostaining for HCN4 and hematoxylin in FCDII tissue. The arrows point to cytomegalic cells expressing HCN4, Scale bars: 2600 μm (FIG. 14A), 100 μm (FIG. 14B) and 50 μm (FIG. 148 inset), 50 μm (FIG. 14C), 50 μm (FIG. 14D) and 20 μm (FIG. 14D inset), and 50 μm (FIG. 14E and inset).

FIGS. 15A-15E depict identification of cytomegalic neurons in patients 3-5 with FCDII. (FIG. 15A, FIG. 15C, and FIG. 15E) Immunostaining for HCN4 and hematoxylin in CDI tissue. The arrows point to cytomegalic cells expressing HCN4. (FIG. 15B and FIG. 15D) Low magnification of the FCDII tissue from patients 3 and 4. The rectangles represent the approximate regions of interest shown at higher magnification in FIG. 15A and FIG. 15C, respectively. Scale bars: 50 μm (FIG. 15A) 1000 μm (FIG. 15B), 100 μm (FIG. 15C), μm (FIG. 15D), and 90 μm (FIG. 15E).

FIGS. 16A-16F depict identification of cytomegalic neurons in patient 7 with FCDII. (FIG. 16A-FIG. 16C) Immunostaining for HCN4 (FIG. 16A and FIG. 16 C, Neuromab antibody) and phospho-S6 (FIG. 16A and FIG. 16B) in FCDII tissue co-stained with DAPI. (FIG. 16E-FIG. 16F) Immunostaining for HCN4 (FIG. 16D and FIG. 16 F. Alomone antibody) and SMI-311 (FIG. 16D and FIG. 16 E) in FCDII tissue co-stained with DAPI Scale bars: 35 μm (FIG. 16A-FIG. 16C) and 40 μm (FIG. 16D-FIG. 16F).

FIGS. 17A-17J depict identification HCN4 overexpression does not lead to convulsive seizures. (FIG. 17A) Confocal images of GFP fluorescence and phospho-S6 immunostaining with DAPI counterstain in coronal sections from 3 months old mice expressing GFP (control) or HCN4 plasmids in the mPFC. Scale bar: 100 μm. (FIG. 17B) Higher magnification and different locations of the fluorescence and staining shown in A. Scale bar: 70 μm. (FIG. 17C) Bar graphs of soma size and phophso-S6 intensity of HCN4-expressing neurons compared to contralateral cells using phopsho-S6 immunostaining for cell detection. Student's t test. (FIG. 17D) Representative current traces in cortical neurons expressing GFP (control) or HCN4. Protocol: conditioning step to −40 mV followed by 10 mV hyperpolarizing steps from −130 to −40 mV. Scale bars: 100 ms/500 pA. (FIG. 17E) Current amplitude (I measured at the end of the trace) versus the voltage in each condition. The grey area indicates the SEM for each curve. Two-way repeated measures ANOVA followed by Tukey post-test. (FIG. 17F) Bar graphs of the RMP of control (GFP) and HCN4-expressing neurons. Student's t test. (FIG. 17G) Representative action potentials upon current injection in HCN4-expressing neurons. Scales: 200 ms/40 mV. (FIG. 17H) Injected current amplitude plotted against the mean number of action potentials in HCN4-expressing neurons. The light gray data are from GFP-expressing neurons from FIG. 3D. The curves were not significantly different with two-way repeated measure ANOVA, followed by Sidak post-test. The grey area outlines the SEM for each curve. (FIG. 17I and FIG. 17G) Representative examples of spikes and spike burst/waves in HCN4-expressing neurons, Scale bars: 5 s/20 μV (FIG. 17I, top), x s/18 μV (FIG. 17I, bottom 5 s/20 μV (FIG. 17J, top), and 0.5 s/20 μV (FIG. 17J, bottom). Data are mean±SEM. **:P<0.001, *:P<0.01, *:P<0.05, and ns: not significant. Exact P values can be found in Table 4.

DETAILED DESCRIPTION

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "CRISPR/Cas" or "clustered regularly interspaced short palindromic repeats" or "CRISPR" refers to DNA loci containing short repetitions of base sequences followed by short segments of spacer DNA from previous exposures to a virus or plasmid. Bacteria and archaea have evolved adaptive immune defenses termed CRISPR/CRISPR-associated (Cas) systems that use short RNA to direct degradation of foreign nucleic acids. In bacteria, the CRISPR system provides acquired immunity against invading foreign DNA via RNA-guided DNA cleavage. CRISPR/Cas9 technology is a biochemical method for genome editing that allows targeted modification by removing, adding or altering sections of the DNA sequence.

A disease or disorder is "alleviated" if the severity of a symptom of the disease or disorder, the frequency with which such a symptom is experienced by a patient, or both, is reduced.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, subcutaneous, oral, aerosol, parenteral, ophthalmic, pulmonary and topical administration.

An "effective amount" or "therapeutically effective amount" of a compound is that amount of compound that is sufficient to provide a beneficial effect to the subject to which the compound is administered. An "effective amount" of a delivery vehicle is that amount sufficient to effectively bind or deliver a compound.

As used herein, "Potassium/sodium hyperpolarization-activated cyclic nucleotide-gated channel 4" or "HCN4" refers to the protein for which the human homolog has the amino acid sequence:

SEQ ID NO: 1

MDKLPPSMRKRLYSLPQQVGAKAWIMDEEEDGEEEGAGGRQDPSRRSIR

LRPLPSPSPSVAAGCSESRGAALGATESEGPGRSAGKSSTNGDCRRFRG

SLASLGSRGGGSGGAGGGSSLGHLHDSAEERRLIAAEGDASPGEDRTPP

GLATEPERPATAAQPAASPPPQQPPQPASASCEQPSADTAIKVEGGAAA

IDHILPEAEVRLGQSGFMQRQFGAMLQPGVNKFSLRMFGSQKAVEREQE

RVKSAGFWIIHPYSDFRFYWDLTMLLLMVGNLIIIPVGITFFKDENTTP

WIVFNVVSDTFFLIDLVLNFRTGIVVEDNTEIILDPQRIKMKYLKSWFV

VDFISSIPVEYIFLIVETRIDSEVYKTARAVRIVRFTKILSLLRLLRLS

RLIRYIHQWEEIFHMTYDLASAVVRIVNLIGMMLLLCHWDGCLQFLVPM

LQDFPHDCWVSINGMVNNSWGKQYSYALFKAMSHMLCIGYGRQAPVGMS

DVWLTMLSMIVGATCYAMFIGHATALIQSLDSSRRQYQEKYKQVEQYMS

FHKLPPDTRQR1HDYVEHRYQGKMFDEESILGELSEPLREEIINFNCRK

LVASMPLFANADPNFVTSMLTKLRFEVFQPGDYIIREGTIGKKMYFIQH

GVVSVLTKGNKETRLADGSYFGEICLLTRGRRTASVRADTYCRLYSLSV

DNFNEVLEEYPMMRKKNSILLHKVQHDLNSGVFNYQENEIIQQIVRHDR

EMAHCAHRVQAAASATPTPTPVIWTPLIQAPLQAAAATTSVAIALTHHP

RLPAAIFRPPPGPGLGNLGAGQTPRHPRRLQSLIPSALGSASPASSPSQ

VDTPSSSSFHIQQLAGFSAPPGLSPLLPSSSSSPPPGACGSPPAPTPST

STAAAASTTGFGHFHKALGGSLSSSDSPLLTPLQPGARSPQAAQPPPPL

PGARGGLGLLEHFLPPPPSSRSPSSSPGQLGQPPGELSLGLAAGPSSTP

ETPPRPERPSFMAGASGGASPVAFTPRGGLSPPGHSPGPPRTFPSAPPR

ASGSHGSLLLPPASSPPPPQVPQRRGTPPLTPGRLTQDLKLISASQPAL

PQDGAQTLRRASPHSSGESVAAFSLYPRAGGGSGSSGGLGPPGRPYGAI

PGQHVTLPRKTSSGSLPPPLSLFGARAASSGGPPLTTAAPQREPGARSE

PVRSKLPSNL

As used herein, "HCN4 disrupting agent" refers to a compound or compounds that eliminate or in combination work to eliminate HCN4 expression or activity or both. In various embodiments, the HCN4 disrupting agent may be an inhibitory polynucleotide such as a small interfering RNA (siRNA) or a small hairpin RNA (shRNA). In various embodiments, the HCN4 disrupting agent may be a CRISPR/Cas9 system that targets and disrupts HCN4. In various embodiments, the HCN4 disrupting agent is HCN4, In various embodiments the HCN4 disrupting agent is delivered by a viral vector which transfects the target cell or cells. In various embodiments the HCN4 disrupting agent is delivered by particles or nanoparticles that enter the target cell or coils.

As used herein. "HCN4 detecting agent" refers to a compound or compounds that bind to and allow the detection of HCN4 in a target area.

As used herein, "Potassium/sodium hyperpolarization-activated cyclic nucleotide-gated channel 4 non-functional" or "$HCN4^{NF}$" refers to an HCN4 polynucleotide or HCN4 polypeptide containing one or more mutations that alone or in combination render the protein non-functional. $HCN4^{NF}$ acts as a dominant negative thus blocking endogenous HCN4 activity. In various embodiments, $HCN4^{NF}$ is an HCN4 polypeptide comprising G480A/G482A.

"Expression vector" refers to a vector comprising a recombinant polynucleotide comprising expression control sequences operatively linked to a nucleotide sequence to be expressed, An expression vector comprises sufficient cis-acting elements for expression; other elements for expression can be supplied by the host cell or in an in vitro expression system, Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

As used herein, the term "epilepsy" refers to a condition in which a person has recurrent seizures. A seizure is defined as an abnormal, disorderly discharging of the brain's nerve cells i.e. neurons), resulting in a temporary disturbance of motor, sensory, or mental function.

As used herein, the term "focal cortical dysplasia type II" or "FCD type II" means a disorder of brain development that leads to focal (or discrete) malformations of the cortex with specific cytoarchitectural alterations including (but not limited to) mislamination and neuron dysmorphogenesis. FCD type 11 can also refer to the malformation itself.

As used herein. "FCM neurons" refers to diseased cells or neurons that display increased HCN4 expression. The term may refer to neurons or cells that are located inside the FCM or outside the FCM and express HCN4 or express increased mTOR activity. FCM neurons or cells contribute to seizure activity and epilepsy.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., rive positions in a polymer ten amino acids in length) of the positions in two sequences are identical, the two sequences are 50% identical; if 90% of the positions (e.g., 9 of 10), are matched or identical, the two amino acids sequences are 90a identical.

A "lentivirus" as used herein refers to a genus of the Retroviridae family. Lentiviruses are unique among the retroviruses in being able to infect non-dividing cells: they can deliver a significant amount of genetic information into the DNA of the host cell, so they are one of the most efficient methods of a gene delivery vector, HIV, SIV, and FIV are all examples of lentiviruses. Vectors derived from lentiviruses offer the means to achieve significant levels of gene transfer in vivo.

By the term "modified" as used herein, is meant a changed state or structure of a molecule or cell of the invention. Molecules may be modified in many ways, including chemically, structurally, and functionally, Cells may be modified through the introduction of nucleic acids.

As used herein, the term "tuberous sclerosis complex" or "TSC" means a genetic disorder resulting from mutations in the gene TSC1 or TSC2 and leads to a spectrum of peripheral and neurological alterations, including, focal malformations of the cortex that are called cortical tubers.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin: talc; excipients, such as cocoa butter and suppository waxes; oils, such as peanut oil, cottonseed oil, safflower oil, sesame oil, olive oil, corn oil and soybean oil: glycols, such as propylene glycol: polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro. Ed., Mack Publishing Co., 1985, Easton, PA), which is incorporated herein by reference.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A" the presence of a molecule containing epitope A (or free, unlabeled A), in a reaction containing labeled "A" and the antibody, will reduce the amount of labeled A bound to the antibody.

A "target site" or "target sequence" refers to a genomic nucleic acid sequence that defines a portion of a nucleic acid to which a binding molecule may specifically bind under conditions sufficient for binding to occur.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

As used herein, "treating a disease or disorder" means reducing the frequency or the severity with which a symptom of the disease or disorder is experienced by a patient, Disease and disorder are used interchangeably herein.

As used herein, the term "treatment" or "treating" encompasses prophylaxis and/or therapy. Accordingly the compositions and methods of the present invention are not limited to therapeutic applications and can be used in prophylactic ones. Therefore "treating" or "treatment" of a state, disorder or condition includes: (i) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition, (ii) inhibiting the state, disorder or condition. i.e., arresting or reducing the development of the disease or at least one clinical or subclinical symptom thereof, or (iii) relieving the disease, i.e. causing regression of the state, disorder or condition or at least one of its clinical or subclinical symptoms.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4.5, 5.3, and 6. This applies regardless of the breadth of the range.

Description

Methods of Treating Disease

Without wishing to be limited by theory, the invention is based in part on the discovery that HCN4 is upregulated in FCM neurons or cells (Example 3). Elimination of HCN4 activity prevented the onset of seizures (Examples 4 and 6). Accordingly, in one aspect the invention provides a method of treating epilepsy in a subject in need thereof, the method comprising contacting a target cell of the subject with an effective amount of an HCN4 disrupting agent, in various aspects and embodiments the methods described herein are applicable to any form of epilepsy. In various embodiments, epilepsy comprises an mTORopathy. In various embodiments, epilepsy results from brain injury or disorders associated with increased mTOR activity including (but not limited to) Cowden syndrome (PTEN mutation), brain trauma, genetic disorders due to mutations in PI3K-AKT-mTOR gene pathways (e.g. AKT in some hemimegalencephaly) or in GATOR gene pathway (e.g. Depdc5), and brain tumors. In various embodiments, epilepsy is related to focal cortical dysplasia type II (FCDII) or tuberous sclerosis complex (TSC).

Various embodiments include the downregulation or elimination of HCN4 in an FCM neuron. In some embodiments, a nucleic acid capable of downregulating endogenous gene expression is introduced, such as by electroporation, transfection, or lenti- or other viral transduction, into the FCM neuron. In one embodiment, the nucleic acid capable of downregulating HCN4 expression is selected from the group consisting of an antisense RNA, antisense DNA, antigomer RNA, siRNA, shRNA, and guide RNA (gRNA), single guide RNA (sgRNA) or crRNAs as part of a with a CRISPR system, zinc-finger nucleases (ZFN), and TALENS (transcription activator-like effector nucleases).

In various embodiments, the HCN4 disrupting agent is $HCN4^{NF}$. Without wishing to be limited by theory, in various embodiments, $HCN4^{NF}$ subunits form heteromers with endogenous HCN4 subunits and render the endogenous HCN4 channel unable to conduct ions. In various embodiments. $HCN4^{NF}$ is delivered in a pharmaceutical composition and crosses the cell membrane. In various embodiments, $HCN4^{NF}$ is transfected into the target cell and is expressed by the target cell.

In various embodiments, the HCN4 disrupting agent is a CRISPR/Cas9 system that targets and disrupts HCN4. In various embodiments, the CRISPR system is a CRISPR interference (CRISPRi) system. In various embodiments, the CRISPR system induces expression of a nucleic acid capable of downregulating or eliminating expression of HCN4 in the cell by editing the gene encoding HCN4. In various embodiments CRISPR/Cas9 system deletes or mutates the gene encoding HCN4 leading to decrease or eliminate HCN4 or induces the expression of a mutant non-functional HCN4. CRISPR/Cas9 systems and CRISPR/Cas9-mediated genetic modification is familiar to a person of skill in the art and discussed in further detail below.

The HCN4 disrupting agent may be delivered by any means known in the art, in various embodiments, the HCN4 disrupting agent is delivered by transfection with a viral vector. The viral vector may be any vector known in the art. In various embodiments, the vector is selected from the group consisting of Sendai viral vectors, adenoviral vectors, adeno-associated viral vectors, retroviral vectors and lentiviral vectors. In various embodiments, the viral vector is an adenoviral vector. In various embodiments, the HCN4 disrupting agent is an adeno-associated viral vector comprising a polynucleotide encoding $HCN4^{NF}$. In various embodiments, the HCN4 disrupting agent is an adeno-associated viral vector comprising a shRNA. In various embodiments, the HCN4 disrupting agent is an adeno-associated viral vector comprising a CRISPR genome editing system including Cas9 and gRNA.

In various embodiments, the HCN4 disrupting agent is delivered in a pharmaceutical composition comprising nanoparticles. In various embodiments the nanoparticles are liposome-templated hydrogel nanoparticles (LHNPs) comprising a polyethyleneimine (PEI) hydrogel core and a cationic DOTAP (1,2-dioleoyl-3-trimethylammonium-propane chloride salt) lipid shell. In certain embodiments, the PEI hydrogel core comprises a cyclodextrin (CD-engrafted PEI (PEI-CD) crosslinked with an adamantine (AD)-engrafted polyethylenimine (PEI)(PEI-AD).

In certain embodiments, a peptide is present (by, for example, conjugation, fusion, and/or physical binding or adsorption) in the lipid shell of the LHNP, so that it is presented at least partially on the surface of the LHNP. For example, mHph1, a cell penetration peptide that enhances gene delivery ability of nanocarriers (Han et at, ACS Nano 2016, 10, 4209; Zhou et al., Biomaterials 2012, 33, 583) can be conjugated to the surface of the lipid shell. In another non-limiting example, mHph3, a modified form of mHph1, consisting of mHph1 fused with a CM18 fragment (Salomone et al., Journal of Controlled Release 2012, 163, 293) can be conjugated to the surface of the lipid shell. In certain embodiments, presenting peptides on the surface of the LHNPs enhances the LHNP's gene delivery ability.

In certain embodiments of the invention, the LHNPs encapsulate at least one molecule. Encapsulated molecules include, but are not limited to, nucleic acids, proteins, drugs, therapeutic agents, and small molecules. In certain embodiments, the encapsulated molecule is Cas9. Encapsulated Cas9 may be in any form known to one of ordinary skill in the art, including but not limited to the protein, DNA. RNA, vector, or plasmid forms. The invention should be construed to include encapsulation of any protein, including but not limited to other CRISPR proteins, for example Cpf1. In various embodiments, the LHNPs encapsulate the HCN4 disrupting agent. In various embodiments, the LHNPs encapsulate a CRISPR system targeting HCN4.

The LHNPs of the present invention should be construed to encapsulate any and all numbers of molecules. For example, 1, 2, 3, 4, 6, 7, 8, 9, 10, and 100 molecules, and any and all numbers in between, can be encapsulated in the LHNPs. In addition, the LHNPs can encapsulate any and all combinations of molecules. For example, the LHNP can encapsulate two molecules such as a protein and a nucleic acid. In certain embodiments, LHNP encapsulates one or more sgRNAs and the Cas9 protein.

Nucleic acids encapsulated by the LHNPs include, but are not limited to, sgRNAs, crRNAs, oligonucleotides, vectors, plasmids, sgRNA expression vectors, and minicircle DNA expression systems. SgRNAs in the present invention can be designed to target any gene or genomic region of interest. In various embodiments, the sgRNAs target HCN4. Further details regarding LHNP nanoparticles are available in Chen et al., Targeted Delivery of CRISPR/Cas9-Mediated Cancer Gene Therapy via Liposome-Templated Hydrogel Nanoparticles, Advanced Functional Materials. Vol. 27(46)(2017).

S In various embodiments, the target cell is a focal cortical malformation (FCM) neuron. In various embodiments, the HCN4 disrupting agent is locally administered to the FCM neuron. In various embodiments, the HCN4 disrupting agent is injected directly into the cortex of the subject such that the HCN4 disrupting agent contacts the FCM neurons in the cortex of the subject. In various embodiments, the method comprises one or several injections of the HCN4 disrupting agent into the brain, in various embodiments into the cortex containing FCM. In various embodiments, several injections are performed during a single surgery.

Methods of Diagnosing Epilepsy

Without being limited by theory, the ectopic expression of HCN4 and the fact that this expression precedes seizures may be applied to diagnose epilepsy or the FCM that are associated with epilepsy. Accordingly, in one aspect the invention provides a method of diagnosing epilepsy in a subject, a method of identifying the FCM to be resected, and a method to assess the efficiency of the manipulations to eliminate or decrease HCN4, the methods comprising administering to the subject an effective amount of an HCN4 detecting agent. In various embodiments, the HCN4 detecting agent is a labeled antibody that binds to HCN4. In various embodiments, the HCN4 detecting agent is a PET tracer that binds to HCN4. In various embodiments, epilepsy comprises an mTORopathy. In another aspect, the invention comprises a method of surgically resecting at least one FCM neuron, the method comprising contacting the FCM neurons with an HCN4 detecting agent, visualizing the HCN4 detecting agent thereby delineating an area comprising the diseased neurons and the FCM, and surgically excising the area.

CRISPR/Cas

Genome editing using programmable nucleases enables precise editing at specific genomic loci, which can be used to remove deleterious mutations or insert protective mutations. To date, there are three major classes of nucleases—zinc finger nucleases (ZFNs), transcription activator-like effector nucleases (TALENs), and clustered, regularly interspaced, short palindromic repeat (CRISPR)-associated nucleases. Of these, CRISPR-associated nucleases have proven to be markedly superior to the others in terms of the ease and simplicity of use.

The CRISPR/Cas system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The Cas9 protein, under direction from the gRNA, binds to its target DNA sequence and cuts both strands of the DNA at a specific locus. This double-stranded DNA break is repaired by either non-homologous end joining (NHEJ) or homology-directed repair (HDR). NHEJ frequently causes small insertions or deletions (indels) at the breakage site that can lead to a frameshift mutation of the protein encoded by the gene. HDR utilizes a repair template that is copied into the gene, thus engineering specific mutations. The CRISPR/Cas system can thereby be engineered to cleave virtually any DNA sequence by redesigning the gRNA.

One example of a CRISPR/Cas system used to inhibit gene expression, CRISPRi, is described in U.S. Publication No: 2014/0068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. The CRISPR-CAS system can also simultaneously target multiple genomic loci by co-expressing a single Cas9 protein with two or more gRNAs, making this system uniquely suited for multiple gene editing or synergistic activation of target genes.

In various embodiments, the nucleic acid capable of decreasing expression of the endogenous gene or a portion thereof is a CRISPR system. In some embodiments, the CRISPR system includes a Cas expression vector and a guide nucleic acid sequence specific for the endogenous gene. In another embodiment, the Cas expression vector induces expression of Cas9 endonuclease. Other endonucleases may also be used, including but not limited to, T7, Cas3, Cas8a, Cas8b, Cas10, Cse1, Csy1, Csn2, Cas4, Cas10, Csn2, Cmr5, Fok1, other nucleases known in the art, and any combination thereof.

The guide nucleic acid sequence is specific for a gene and targets that gene for Cas endonuclease-induced double strand breaks. The sequence of the guide nucleic acid sequence may be within a locus of the gene. In various embodiments, the target gene is HCN4. In one embodiment, the guide nucleic acid sequence is at least 10, It, 12, 13, 14, 15, 16, 17, 18, 19, 20, 21, 22, 23, 24, 25, 26, 27, 30, 31, 32, 33, 34.35, 36, 37, 38, 39, 40 or more nucleotides in length.

The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the following examples are here described.

Animals

All experiments were performed on CD-1 (Charles River), an outbred strain of mice of either gender. All the experiments used age-matched animals for control and experimental conditions.

Human Tissue Sample

Human tissue was obtained from different sources: directly from the surgery room or from the Tuberous sclerosis Alliance. Freshly resected tissue was rapidly frozen in 2-Methylbutane (isopentane; Acros Organics MS: AC12647-0010) at <−80° C., rapidly frozen in liquid nitrogen and then stored at −80° C. (for immunoblotting and immunostaining), or fixed in 10% formalin (for immunohistochemistry). The sample from the TSA alliance was provided as frozen. Freshly frozen tissue was sectioned (13 μm) via a cryostat and fixed in 4% PFA for 2 minutes before immunostaining. Patient information is provided in Table 1.

In Utero Electroporation and Plasmids

Each DNA plasmid was diluted in sterile PBS (pH 7.4) to a final concentration of 1.5-3 μg/μl (specific concentrations below). About 1 μl of DNA solution containing 0.1% fast green was injected into the lateral ventricle of E15.5±0.5 fetuses with a glass pipette. After injection, PBS soaked tweezer-type electrodes (model 520, BTX) were positioned on heads of the fetuses across the uterine wall and 6 square-pulses (42V, 50 ms duration, 950 ms intervals) were applied using a pulse generator (ECM830, BTX). Mice were prescreened for successful electroporation on a fluorescence enabled stereo microscope (SZX16, Olympus) prior to recruitment for EEG monitoring. To generate epilepsy-associated FCM, a DNA solution composed of pCAG-RhebS16H (Rheb$^{CA}$, 2 µg/µl) and pCAG-tdTomato (1 µg/µl) was injected in half of all fetuses while pCAG-GFP (3 µg/µl) containing solution was injected in the remaining littermates as controls. To silence FCM neurons, pCAG-Kir2.1-T2A-tdTomato (2 µg/µl)+pCAG-Rheb$^{CA}$ (2 µg/µl) was injected in half of the fetuses while the remaining half received pCAG-Rheb$^{CA}$ (2 µg/µl)+pCAG-GFP (2 µg/µl) as controls.

Seizure Detection and Analysis

Animals were randomly assigned an arbitrary identification number without knowing the experimental condition before implanting dual independent channel EEG electrodes (FIG. 18) for identification after the double-blind analyses. Six-pin EEG headmounts (made inhouse) were attached with two stainless steel machine screws and a dab of cyanoacrylate to the skulls of electroporated animals of >2 months of age. After one week of recovery, EEG preamplifiers were attached to the implants and to an electrical commutator (Pinnacle Technology Inc.) to allow tethered recordings from freely moving animals. EEG (sampled at 400 Hz) were recorded with digital video continuously for 7 consecutive days for each animal. Epileptiform activity was analyzed post hoc, while blinded to the condition, using Sirenia Seizure Pro software (Pinnacle Technology Inc.) to identify possible seizure epochs, An automated line length search method was applied to all recorded EEG channels with the threshold set at 500) length/sec using a 10 second search window with a 0.5 second sliding window, Identified episodes were verified manually with video inspection. Convulsions that reached Racine stage 3-5, from forelimb clonus to rearing and falling with forelimb clonus, were counted as a seizure. Seizure duration was defined from the onset of convulsion to cessation of all motor movement. Data are reported as average number of seizures per day. Power spectrums, with and without temporal component, were analyzed for each epoch, from the onset of convulsion to the cessation of motor movements. For preictal (baseline) power spectrum analyses, with and without temporal component, corresponding time window 60 seconds before convulsion onset was used (Pinnacle Seizure Pro software).

Brain Slice Preparation, Immunohistochemistry, and Analysis

Mice were deeply anesthetized with pentobarbital (50 mg/kg) and perfused transcardially with ice cold phosphate buffered saline (PBS, pH 7.4) followed by ice cold paraformaldehyde (PFA, 4%). Perfused brains were also drop fixed in 4% PFA for an additional hour after removal from the skull. Fixed brains were cryoprotected with 30% sucrose in PBS overnight at 4° C. and serially sectioned into 50 µm thick sections using a freezing microtome. Sections were blocked for 1 hour at room temperature in blocking buffer consisting of 2% BSA and 0.3% Triton X-100™ in PBS, Floating sections were incubated overnight at 4° C. in primary antibodies diluted in blocking buffer. Following 3 washes in PBS and an additional 15 min in blocking solution at room temperature, sections were then incubated with secondary antibodies at 1:1000 dilution for 2 hours at room temperature, ProLong™ Gold antifade reagent (Life Technologies) was used to mount and preserve stained sections. While blinded to the experimental conditions. Z-stack images were acquired using a fluorescence confocal microscope (FV1000, Olympus) with a 20× dry objective (N.A. 0.75, Olympus) and reconstructed using Imaris 4.0 (Bitplane AG) and Photoshop CS6. Fluorescence intensities and cell sizes were quantified using ImageJ 1.39t (Freeware, Wayne Rasband. NIH). Cell size was quantified by averaging 15 brightest fluorescently tagged cells per animal. Immunofluorescence of phospho-S6 in the same 15 brightest cells and HCN4 in all the fluorescently labelled cells was quantified using integrated fluorescence.

The list of antibodies is detailed in Table 0.3. Antibodies were extensively used and validated by previous studies. In addition, the specificity of the HCN4 antibody was further confirmed by siRNA-mediated knockdown in vitro (FIGS. 10A-10E) and exclusive immunoreactivity in neurons electroporated with an HCN4 overexpression plasmid and not in non-electroporated neurons in the vicinity (FIGS. 11A-11B).

Acute Slice Preparation and Whole Cell Recording.

1-5-week-old mice were used for acute slices. Tissue was dissected and sliced in ice cold artificial cerebral spinal fluid (aCSF)oxygenated with 95% $O_2$/5% $CO_2$. The aCSF contained (all in mM): 124 NaCl, 3 KCl, 1.25 $NaH_2PO_4$, 1 $MgSO_4$, 26 $NaHCO_3$, 10 Dextrose, 2 $CaCl_2$, 0.4 ascorbate, 4 Na-Lactate, 2 Na-Pyruvate (290±5 mOsm/kg, pH 7.2). Coronal sections (350 µm) were prepared using a vibratome (Vibratome 1000). Sections were incubated in aCSF at 32° C. for 45 minutes before returning to room temperature (25° C.) where they were kept for 8 to 10 hours during experimentation. Fluorescent neurons in the mPFC were visualized using epifluorescence on an Olympus BX51WI microscope with a 40× water immersion objective (Olympus, LUMPlanFL/IR). Whole-cell recordings were performed at 28° C. using pulled glass pipettes (4-7 ΩM) filled with internal solution (in mM: 110 K-gluconate, 4 KCL, 10 HEPES, 10 di-tris-phosphocreatine, 4 Mg-ATP, 0.3 Na-GTP). Recordings were acquired with an amplifier (Axopatch 200B, Molecular Devices), The resting membrane potential was recorded within the first 10 seconds after achieving whole, cell configuration in current-clamp mode, while the cell is at rest without any holding current. The membrane conductance was calculated using the average membrane potential change from ten hyperpolarizing current injections of −500 pA in current-clamp mode when the cell is at rest. The action potential half width was calculated at half of the peak amplitude of a single action potential induced by current injection. The action potential firing threshold was defined as the membrane potential at which the first derivative of an action potential in current-clamp mode achieves 10% of its peak velocity (dV/dt). The action potential input-output curve was generated by injecting positive current in current-clamp mode from 0 to 2 nA at 100 pA increments for 500 msec.

IMR32 (Human Neuroblastoma) Cell Lie and Immunoblotting

IMR-32 cells were grown at 37° C. with 5% $CO_2$ in Eagle's Minimum Essential Medium supplemented with 10% fetal bovine serum and 1% penicillin-streptomycin. Cells were plated in 6-well culture plates and transfected when they reached ~70-90% confluence, Transfection of the HCN4 overexpression plasmid was done using Lipofectamine™ 3000 reagent (Invitrogen) and transfection of the Stealth RNAi siRNAs against HCN4 [Invitrogen: HSS1125216, HSS115218, HSS173331 (human) MSS221131 (mouse)] was done using Lipofectamine™ RNAiMAX reagent (Invitrogen) according to the manufacturer's protocol. Cells were collected 48 hours after transfection for western blotting. Briefly, cells were lysed in lysis buffer (150 mM NaCl, 40 mM Tris-HCl, 1 mM EDTA, and 1% Triton X-100™ in deionized water+phosphatase and protease cocktail inhibitors) and resolved with SDS-PAGE. Samples were then transferred onto PVDF membranes, blocked in 5% milk, and incubated with primary antibodies (concentrations of primary antibody are listed in Table 3)

overnight. HRP-conjugated anti-rabbit or anti-mouse were used as secondary antibodies.

RNA Isolation and qRT-PCR from Rbeb$^{CA}$- and GFP-Electroporated Cortices

RNA was extracted using standard Trizol protocol from microdissected cortex of 3-4 months old mice containing Rheb$^{CA}$ or GFP neurons after E15 IUE. Complementary DNA (cDNA) was prepared using the RT$^2$ Nano PreAMP cDNA Synthesis Kit (SA Biosciences). cDNA (12 μl), combined with the FastStart Universal SYBR Green Master (Roche), was loaded per well on the Mouse Neurogenesis PCR Array (384-well plate: SA Biosciences). For qRT-PCR, 2.12 μg of RNA was mixed with dinucleotide triphosphates, random primers (Invitrogen). cDNA was subjected to PCR with primers to mouse

```
Hcn1
(F, CAAATTCTCCCTCCGCATGTT (SEQ ID NO: 2);
R, TGAAGAACGTGATTCCAACTGG (SEQ ID NO: 3)),

Hcn2
(F, CCGGCGTCAACAAGTTCTC (SEQ ID NO: 4);
R, TGCCCACGGGAATGATAATGA (SEQ ID NO: 5)),

Hcn4
(F, GGCGGACACCGCTATCAAA (SEQ ID NO: 6);
R, TGCCGAACATCCTTAGGGAGA (SEQ ID NO: 7)),

Vegf
(F, AGCCGAGCTCATGGACGGGT (SEQ ID NO: 8);
R, CTGTCGTGGGTGCAGCCTGG (SEQ ID NO: 9)),
and Gapdh
(F, ACCACCATGGAGAAGGC (SEQ ID NO: 10);
R, GGCATGGACTGTGGTCATGA (SEQ ID NO: 11)).
```

Culture of E18 Cortical Neurons Followed by Nucleofection

The cortex of E18 pups was dissected out to prepare primary neuronal culture as described earlier. Once in cell suspension, neurons were nucleofected using the Mouse Neuron Nucleofector Kit VPG-1001 (Lonza) and following the manufacture's instructions. Western blot analysis was performed 7 days following nucleofection.

Statistical Analyses

All analyses were conducted blindly knowing only the arbitrarily assigned animal ID (independent of electroporation condition). Statistical tests and plots were performed using Prism 7 (GraphPad Software, Inc.). Statistical significance was determined using, Student's t-test (two-tailed, paired or unpaired), two-way ANOVA (repeated measures, with Sidak's or Tukey multiple comparisons post-test, Wilcoxon matched-pairs signed rank test, Mann Whitney U test (two-tailed), and Pearson correlation, with P<0.05 for significance for all experiments. Data are presented as mean±SEM.

Example 1: Silencing FCM Neurons Decreases Seizure Activity

To investigate the mechanisms of seizure generation in FCM, a mouse model that recapitulates the focal nature of the cortical malformation and the cellular mosaicism of human FCDII and TSC brains was used, To generate this model, in utero electroporation (IUE) to induce mTOR hyperactivity in pyramidal neurons in a limited cortical area (FIG. 1A) was used. IUE at embryonic day (E) 15 specifically target radial glia that generate layer 2/3 pyramidal neurons (FIG. 1B). To increase mTOR activity, a constitutively active mutant Rheb (Rheb$^{CA}$), the canonical mTOR activator was expressed (FIG. 18). A fluorescent protein (GFP or tdTomato) was co-expressed to label neurons. These mice developed a singular FCM in the medial prefrontal cortex (FIG. 1C) that displayed a pathology resembling that of human FCM, including the presence of misplaced and cytomegalic Rheb-expressing neurons that are interchangeably called FCM neurons (FIG. 1 and FIG. 1E). These FCM neurons showed a significant increase in soma size and immunoreactivity for phosphorylated protein S6 (phospho-S6), a read-out of mTOR activity, compared to control neurons in mice electroporated with GFP only (FIG. 1F and FIG. 1G). Mice containing FCM were visually observed to develop convulsive seizures by postnatal day (P) 21. To better characterize the seizures, epidural electroencephalography (EEG) recordings combined with video monitoring for 5-7 consecutive days in 3-4 months old mice were obtained. Mice containing FCM exhibited recurrent, Racine grade 4-3 seizures with classical interictal, tonic, clonic, and postictal periods (FIGS. 1H and 1I).

Using a mouse model of FCM, it was previously reported that FCM neurons display depolarized resting membrane potentials (RMP) compared to their control counterparts and are therefore closer to the threshold for generating action potentials. It was thus examined whether silencing PCM neurons without normalizing their morphological abnormalities, which could contribute to seizure generation, would limit the incidence of seizures. To do this, inwardly rectifying potassium channels Kir2.1 that are expected to hyperpolarize neurons expressing these channels as well as decrease their membrane resistances was overexpressed. Using E15 IUE, Kir2.1 was co-expressed with Rheb$^{CA}$ (FIG. 2A), in the control condition, GFP was co-electroporated with Rheb$^{CA}$. Kir2.1 expression in Rheb$^{CA}$ neurons did not prevent the formation of FCM (FIGS. 2A and 2B) and did not interfere with MTOR hyperactivity as shown by quantification of soma size and phospho-S6 immunofluorescence, respectively (FIG. 2C). Furthermore, patch clamp recordings of Rheb$^{CA}$ neurons in acute slices from P21 to P35 validated that Kir2.1 expression did not alter membrane capacitance (a read-out of soma size), but it significantly hyperpolarized Rheb$^{CA}$ neurons and increased their membrane conductance (FIG. 2D). The properties of current-induced action potentials, including half-width and threshold, were unaltered by Kir2.1 expression (FIGS. 2E and 2F), but consistent with the changes in RMP and membrane conductance, larger current injections were required for the generation of action potentials Kir2.1-expressing FCM neurons (FIG. 2G). This resulted in a significant shift in the input (injected current amplitude)-output (number of action potentials) curve (FIG. 2H), Thus, expressing Kir2.1 renders FCM neurons less excitable, in part via hyperpolarizing their RMP further away from the action potential threshold. Importantly, mice overexpressing Kir2.1 in FCM neurons displayed a significant decrease in seizure frequency (from a mean of 4.5 to 0.5 seizures per day) without affecting seizure duration (FIGS. 2I and 2J). Collectively, these data show that alterations in the electrical properties of FCM neurons are necessary for seizure initiation and that silencing these neurons is sufficient to alleviate seizures.

Example 2: FCM Neurons Abnormally Express HCN Channels Leading to Depolarized RMP and cAMP Sensitivity Next were examined the electrical properties of FCM neurons using patch clamp recordings in acute brain slices from P26-P42 mice. As previously reported, it was confirmed that FCM neurons displayed significantly depolarized RMPs and increased conductance compared to control neurons in littermate mice expressing only GFP (FIG. 3A). Consistent with an increased conductance, there was a significant shift in the input (injected current from their RMP)-output (# of action potentials) curve, suggesting that Rheb$^{CA}$ neurons are less likely to generate action potentials upon depolarizations (FIGS. 3C and 3D). Using hyperpolarizing current step, one unexpected observation was the present of a robust "sag" response in Rheb$^{CA}$ neurons that was either minimal or mostly not present in control neurons (FIG. 3E). Such a sag response suggests the presence of HCN channels. Under control conditions, HCN channels are primarily expressed in deep layer neurons but not in superficial layer (2/3) neurons, which are the neuronal population targeted by IUE at E15, In addition, HCN currents are known to control neuron RMPs and may thus contribute to the depolarized RMP in Rheb$^{CA}$ neurons, Preferentially these channels were focused on. To validate that these sags were due to the presence of HCN channels, Rheb$^{CA}$ neurons in the presence of the HCN channel blocker, zatebradine were recorded. Zatebradine eliminated the sag response in Rheb$^{CA}$ neurons (FIG. 3F. Using voltage-clamp, Sot ms-long hyperpolarizing voltage-steps (from −40 to −130 mV) to activate HCN channels (FIG. 3O) was applied, Rheb$^{CA}$ neurons displayed large hyperpolarization-activated inward currents that were much larger than in the control neurons (FIGS. 3G and 3H). These inward currents displayed a slow activation kinetics resembling that of HCN currents requiring a 3 s-long voltage pulse to reach full amplitude (FIGS. 9A-9B) and were significantly reduced in the presence of zatebradine (FIGS. 3G and 3H). The increased hyperpolarization-induced inward currents were nevertheless not fully blocked by zatebradine presumably due to an increase in the amplitude of inwardly rectifying K currents (Kir) in Rheb$^{CA}$ neurons compared to control due to the cell size increase (FIGS. 3G and 3H). As evident on the current-membrane potential curves (FIG. 3H) and further quantified, zatebradine shifted RMP of cells to hyperpolarized values similar to those of control neurons (FIG. 3I). To quantify the h current amplitudes, the amplitude difference (ΔI) between the onset and the end of the current trace using a 500 ms-long voltage step (see dotted line and th in FIG. 3G) was measured. Zatebradine significantly reduced these ΔI and there was no residual inward current at −90 mV (FIG. 3). Throughout, Ih current amplitude will then be measured as ΔI at −90 mV using this method. Consistent with the normalization of RMP with zatebradine, larger h currents were associated with more depolarized resting membrane potentials in Rheb$^{CA}$ neurons (FIG. 3K). The amplitude of the h currents was also dependent on the amount of electroporated Rheb$^{CA}$ plasmid and thus mTOR activity level (FIGS. 9A-9B). HCN channels contribute to the generation of rhythmic firing in neurons and heart cells and they display different sensitivity to intracellular cAMP levels. Thus examined was whether increasing cAMP in Rheb$^{CA}$ neurons would be sufficient to trigger spontaneous, repetitive firing independently of depolarizations. Then was both applied a well-characterized cell-permeable adenylate cyclase activator, forskolin, to increase in intracellular cAMP in acute brain slices containing Rheb$^{CA}$ neurons. When recorded at the resting membrane potential, all Rheb$^{CA}$ neurons were depolarized by forskolin and 4/9 neurons generated repetitive action potentials (FIGS. 3L and 3M). This effect did not occur in control superficial layer neurons (FIGS. 3L and 3M), which express very few or no HCN channels. Collectively, these data indicate that Rheb$^{CA}$ neurons express ectopic HCN channels and the abnormal presence of these channels is responsible for the depolarized resting membrane potentials of Rheb neurons and their repetitive firing upon increases in intracellular cAMP.

Example 3:—Ectopic HCN4 Expression in FCM Neurons

HCN channels are encoded by four genes, HCN-4, with different expression patterns throughout the brain. In the adult cortex, deep layer pyramidal neurons predominantly express HCN1 and low levels of HCN2 at the protein level, HCN3 and HCN4 display weak, diffuse expression in the cortex. HCN4 expression has been found in neuronal cell bodies scattered in the cortex that may be GABAergic neurons, but it is nearly absent in the cortex of young adult mice. Furthermore, in situ hybridization and immunoblotting detect low HCN3 and HCN4 mRNA levels in the adult cortex. HCN4 followed by HCN2 channels are the most sensitive to intracellular cAMP levels while HCN1 channels display low sensitivity, HCN1-4 in 2 months old mouse brain sections containing FCM were thus immunostained. Consistent with previous studies, intense HCN1 staining predominantly in apical dendrites of deep layer neurons and weak, diffuse HCN2 staining in the cortex (FIGS. 4A and 4B) was identified. However, no changes in HCN1 and HCN2 staining pattern in the ipsilateral cortex containing FCM compared to the contralateral cortex as well as no staining in Rheb$^{CA}$ neurons was found (FIGS. 4E and 4F). No HCN3 staining was found in the cortex. However, strong HCN4 immunostaining was identified in the cortex containing Rheb$^{CA}$ neurons using two different antibodies against HCN4 (FIGS. 4C and 4D). There was no expression of HCN4 in neurons of the contralateral hemisphere suggesting that aberrant HCN channel expression does not result from recurrent seizures. One of the antibodies (Alomone Labs) was previously validated in vivo in conditional knockout mice. In addition, the specificity of both HCN4 antibodies was further confirmed by siRNA-mediated HCN4 knockdown in vitro followed by HCN4 immunoblotting (FIGS. 10A-10E) and exclusive immunoreactivity in neurons electroporated with an HCN4 overexpression plasmid and not in non-electroporated neurons in the vicinity (FIGS. 11A-11B). About 85% of Rheb$^{CA}$ neurons displayed HCN4 immunoreactivity that decorated their soma, dendrites, and axons (FIGS. 4C, G, and I). Finally, GFP-expressing cells in mice electroporated with GFP instead of Rheb$^{CA}$ did not display HCN4 expression (FIGS. 4H and 4I). Thus, Rheb$^{CA}$-expressing neurons display selective HCN4 expression that was absent in control pyramidal neurons.

Example 4:—Abnormal HCN4 Expression is mTOR-Dependent and Precedes Seizure Onset To assess whether increased mTOR activity was responsible for the abnormal expression of HCN4, mice were treated with the mTOR inhibitor rapamycin using the treatment paradigm (1 mg/kg every 49 hours from P1 to 2 months of age) that prevented FCM and the development of seizures. Rapamycin treatment prevented the expression of HCN4 in Rheb$^{CA}$ neurons compared to vehicle-treated mice (FIGS. 5A-5C), mTOR is a master regulator of protein translation, but can also lead to increases in mRNA, it was thus examined whether Hcn4 mRNA was increased in Rheb$^{CA}$-compared to GFP-electroporated cortices from 3-4 months old mice. Quantitative RT-PCR was performed for Hcn1, 2, and 4 as well as Vegf which is increased in hyperactive mTOR conditions. The levels of Hcn1, 2 and 4 mRNA were unchanged while the levels of Vegf mRNA was significantly increased (FIG. 5D). Considering that HCN channel expression has been shown to be up- or down-regulated by seizures, it was examined whether Rheb$^{CA}$ neurons would express HCN during postnatal cortical development prior to the onset of convulsive seizures that were visible in >P21 mice. Recordings in slices from P8-P12 mice showed that Rheb$^{CA}$ neurons displayed zatebradine-sensitive HCN currents that were significantly greater than in control GFP neurons recorded in littermate mice (FIGS. 5E-5G). In addition, there was a significant increase in the HCN currents in Rheb$^{CA}$ neurons during development from P6-12 to P28-P42 but no significant change in control neurons (FIG. 5H). These data indicate that mTOR hyperactivity drives aberrant expression of HCN4 in FCM neurons prior to the onset of convulsive seizures.

Example 5: HCN4 is Abnormally Expressed in Human TSC and FCDII Neurons

Data presented above indicate that HCN4 channels confer a spiking advantage in Rheb$^{CA}$ neurons that otherwise would not be able to generate repetitive firing upon cAMP stimulation. To examine whether abnormal HCN4 expression occurs in patients with FCM, cortical tissue from nine patients that underwent surgery for epilepsy due to FCM were obtained. Seven patients had the histopathological diagnosis of FCDII and two patients had TSC. Patients had FCM detected on MRI and underwent EEG with a combination of subdural grid and depth electrodes prior to FCM resection. Patients were identified as FCDII post-surgery based on pathological examination of the H&E-stained resected tissue and identification of hallmarks of FCDII, including cortical dyslamination and the presence of cytomegalic neurons. In addition, for tissue used for immuno-fluorescence (N=3), the presence of cytomegalic neurons with hyperactive mTOR was confirmed using immunostaining for SMI 311 and phospho-S6, respectively (FIGS. 12A-12D and FIGS. 6D-6E for FCDII; FIG. 13 and FIG. 7D for TSC). SMI-311 is a pan-neuronal neurofilament (NF) that is accumulated in the soma and dendrites of dysmorphic neurons in human and murine FCD and is considered a marker of these neurons. Dysmorphic SMI 311-immunopositive neurons expressed the neuronal markers, NeuN and neurofilament-light chain (NFL), increased immunoreactivity for phospho-S6 compared to normal-appearing, surrounding cells (FIGS. 12A-12D and FIG. 13). In all nine tissue samples, HCN4 immunoreactivity in cytomegalic cells was identified and no or weak staining in surrounding cells (FIGS. 6A-6D, FIGS. 14A-14D, and FIGS. 16A-16F) for FCDII and FIGS. 7A-7E for TSC). HCN4-positive fibers were visible in some samples (FIGS. 6A-6D) and may correspond to either processes of diseased neurons or thalamic inputs or both. HCN4 immunostaining was performed with the two different antibodies (but not for all samples) that was tested in mice as indicated on the FIGS. Cytomegalic cells expressing HCN4 displayed enlarged nuclei as shown by hematoxylin staining (in paraffin-embedded samples, FIG. 6A). In addition, cells displaying HCN4 immunoreactivity expressed phospho-S6 (FIG. 6D for FCDII and FIGS. 7A-7C for TSC) and SMI 311 identifying them as cytomegalic, diseased neurons (FIG. 6E and FIG. 7D). Collectively, these data show that both mouse FCM neurons and dysmorphic human neurons from TSC and FCDII patients display abnormal expression of HCN4 channels.

Example 6: Overexpressing HCN4 in Control Neurons does not Lead to Convulsive Seizures HCN channels contribute to the generation of rhythmic firing in neurons and heart cells. In addition, data in FIGS. 3A-3M showed that HCN4 channel expression drove firing in Rheb$^{CA}$ neurons upon cAMP stimulation. It was then examined whether ectopic expression of HCN4 alone was sufficient to trigger convulsive seizures. To do so, a plasmid encoding HCN4 was expressed together with tdTomato or GFP using WE at E15 to target L2/3 neurons. As reported above. HCN4 antibodies detected HCN4 immunostaining selectively in pyramidal neurons electroporated with HCN4 plasmid (FIGS. 11A-11B). At 5 months of age, neurons overexpressing HCN4 were located in L2/3 as in control condition and did not display increased soma size or increased phospho-S6 staining compared to contralateral layer 2/3 neurons (FIGS. 17A-17C). In acute slices of P21-43 mice. HCN4-overexpressing neurons displayed larger hyperpolarization-activated inward currents and mean depolarized RMP compared to control neurons (FIGS. 17D-17E). HCN4-overexpressing neurons display a mean input-output (# of action potentials) curve similar to that of control neurons although firing is detected earlier (FIGS. 17F-17G). One of 17 recorded HCN4-overexpressing neurons displayed spontaneous firing at its RMP. Next 7-day long video-EEG recordings of 2 to 3 month-old mice expressing HCN4 channels was performed. None of the HCN4-expressing mice displayed tonic-clonic seizures (n=7/7. Nonetheless, 5/7 mice displayed epileptiform discharges containing spikes, spike trains, and waves on the ipsilateral side that were absent both on the contralateral side and in GFP-expressing mice (FIGS. 17H-17J). These data show that HCN4 overexpression in control pyramidal neurons of the mPFC without morphological alterations typical of Rheb$^{CA}$ neurons was not sufficient to trigger convulsive seizures.

Example 7: Blocking HCN4 Activity Prevents the Establishment of Epilepsy

To then address whether the ectopic expression of HCN4 channels in Rheb$^{CA}$ neurons contributed to seizure generation in FCM-expressing mice, HCN channel activity in vivo were blocked. To do so, nonfunctional HCN4 (HCN4$^{NF}$) subunits that were generated by adding two mutations into HCN4 were expressed. HCN4$^{NF}$ subunits are expected to form heteromers with endogenous HCN4 subunits and render the endogenous HCN4 channel unable to conduct ions, thus acting as dominant-negative. Indeed, both the sag responses observed in current clamp and the h currents recorded in voltage clamp in Rheb$^{CA}$ neurons were eliminated in Rheb$^{CA}$ neurons that co-expressed HCN4$^{NF}$ (FIGS. 8A and B). Furthermore. HCN4$^{NF}$ expression significantly normalized the resting membrane potentials of Rheb$^{CA}$ neurons (FIG. 8C) similarly to what was shown with the HCN channel blocker zatebradine in FIG. 3. Similar to the experiments with Kir2.1, expressing HCN4$^{NF}$ in Rheb$^{CA}$ neurons did not interfere with mTOR hyperactivity as measured by phospho-S6 immunofluorescence and soma sixe (FIG. 8D and SE). HCN4$^{NF}$ expression in Rheb$^{CA}$ neurons did not alter the properties of action potentials (FIG. 8F) or the input-output curve (FIGS. 8G and H). Thus, expressing HCN4$^{NF}$ in Rheb$^{CA}$ neurons did not alter their ability to generate actions potentials, but it hyperpolarized them back to control levels and blocked the activity of endogenous HCN4 channels. Finally, a 7-day long continuous video-EEG monitoring of mice containing $Rheb^{CA}$ neurons expressing $HCN4^{NF}$ revealed that these mice had no seizures whereas littermate mice containing $Rheb^{CA}$ neurons (without $HCN4^{NF}$) displayed a mean of three daily, convulsive seizures (FIGS. 8I and 8J). Together, these data indicate that the abnormal expression of HCN4 channels in FCM neurons are necessary for generating seizures and blocking HCN4 channels is sufficient to decrease seizure activity Example 8: Discussion In light of previous data reporting depolarized RMPs of $Rheb^{CA}$ neurons, it was thought that Rheb neurons may be more excitable and thus trigger seizures. To test this, Kir2.1 channels were expressed in $Rheb^{CA}$ neurons to hyperpolarize them and examine whether this would limit seizure activity. Kir2.1 expression indeed hyperpolarized the RMPs of $Rheb^{CA}$ neurons and increased their membrane conductance leading to a right shift in the input-output curve without preventing increased cell size, mTOR hyperactivity, and misplacement. These data show that $Rheb^{CA}$ neurons expressing Kir2.1 were thus less excitable by being hyperpolarized and less responsive to depolarization. As a result of this manipulation, mice had significantly fewer seizures per day, suggesting that alterations in $Rheb^{CA}$ neurons' electrical properties contribute to seizures. Using whole cell patch clamp recordings to examine electrical properties, it was confirmed that $Rheb^{CA}$ neurons have depolarized RMPs and are thus closer to the threshold for generating action potentials. However, they also displayed increased conductance and thus required a larger depolarizing current injection to reach firing threshold, hence $Rheb^{CA}$ neurons were less excitable in response to depolarization than control neurons. These findings initially seemed to contradict the conclusion from the Kir2.1 experiment that $Rheb^{CA}$ neurons could trigger seizures. However, it was further identified the aberrant expression of HCN currents that provided an explanation for the unusual, increased likelihood of $Rheb^{CA}$ neurons to generate action potentials independent of depolarizing inputs, but dependent on intracellular cAMP levels as further detailed below. In young adults, $Rheb^{CA}$ neurons expressed larger inward currents than in controls, including a combination of HCN- and presumed Kir-mediated currents. Outward currents could not be examined in $Rheb^{CA}$ neurons due to poor space clamp leading to unclamped firing upon depolarizing voltage pulses. Due to the large increase in $Rheb^{CA}$ neuron size, it was not surprising to find larger Kir-mediated currents, which are well-known to be expressed in control layer 2/3 pyramidal neurons as G protein inwardly rectifying K channels. However, finding HCN-mediated currents was surprising because control layer 2/3 pyramidal neurons are not known to express such currents, as confirmed here. HCN channels, in particular HCN2 and HCN4, are sensitive to cAMP levels with higher cAMP levels leading to increased HCN-mediated currents. Considering that the levels of cAMP increases in developing hippocampal neurons (doubled from P6 to P15) and could be altered in disease condition, it is conceivable that the increase in HCN currents could also be due to increased cAMP levels in $Rheb^{CA}$ neurons compared to control neurons. cAMP levels in $Rheb^{CA}$ neurons were not directly measured. However, using immunostaining it was identified that the selective expression of HCN4 that was not present in control neurons and expressing $HCN4^{NF}$ led to a significant reduction of HCN-mediated current. These data suggest that HCN-mediated currents in $Rheb^{CA}$ neurons are primarily due to the ectopic expression of HCN4 channels independent of changes in cAMP levels. With respect to neuron excitability, it was found that increasing intracellular cAMP levels with forskolin was sufficient to trigger the firing of $Rheb^{CA}$ neurons, Therefore, although $Rheb^{CA}$ neurons have an increased membrane conductance and require more current injection to reach firing threshold, they are more depolarized and an increase in intracellular cAMP levels, as opposed to excitatory input-induced depolarization, acts as the trigger to induce $Rheb^{CA}$ neuron firing. These data show an unanticipated and novel mechanism of excitability that is consistent with a significant decrease in the excitatory drive (i.e., frequency of spontaneous excitatory synaptic inputs) onto $Rheb^{CA}$ neurons. Identifying a cAMP-dependent excitability in $Rheb^{CA}$ neurons is tantalizing because cortical pyramidal neurons receive multiple inputs that activate receptors leading to cAMP increases. These inputs include noradrenergic and dopaminergic innervation from the locus coeruleus and the ventral tegmental area (e.g., Gs-coupled β1- and β2-adrenergic receptors and D1 and D5 receptors). Noradrenaline or dopamine released from these inputs could thus contribute to cAMP increases and HCN4 channel activation that would lead to firing and seizures it is also conceivable that inhibitors of these receptors, preventing increases in intracellular cAMP levels, may alleviate seizure activity.

Regarding the identity of the HCN channels expressed in $Rheb^{CA}$ neurons, it was found the selective expression of HCN4 channels by immunostaining. It is possible that $Rheb^{CA}$ neurons also acquire HCN1 or HCN2 channels at densities below detection levels for immunostaining. Nevertheless, the important finding was the fact that HCN4 expression was absent in control pyramidal neurons in these sections and has not been reported in cortical pyramidal neurons in young adult mice despite the presence of mRNA neurons. It was found that about 85% of the $Rheb^{CA}$ neurons labeled with tdTomato displayed HCN4 immunoreactivity. Considering that every recorded $Rheb^{CA}$ neuron expressed HCN-mediated currents, albeit with different amplitude, it is possible that HCN4 expression in a subset of $Rheb^{CA}$ neurons was below the detection limit for immunostaining. Finding HCN4 channels in neurons that normally do not express these channels may seem surprising. However, as shown in the developing hippocampus, HCN4 is strongly expressed perinatally in the cortex and is dramatically decreased in young adults (P30). HCN4 channels are thus intrinsic to cortical neurons during development. Considering HCN4 expression was mTOR-dependent, and mTOR increases protein translation, it is conceivable that the ectopic HCN4 expression results from increased translation of mRNA already present in pyramidal cortical neurons. Consistent with this idea is that the transcript levels for HCN4 was unchanged in $Rheb^{CA}$-expressing cortical neurons. This is also consistent with the fact that published gene arrays performed in cortical tuber samples from individuals with TSC found no changes in Hcn4 mRNA levels.

These findings add to a large body of literature on HCN expression and seizures. Indeed, several studies have reported alterations in the expression of HCN, in particular, HCN1 and HCN2, in different types of epilepsy in both mice and humans, One recent study reported that blocking HCN1 channel activity prevented absence seizures, suggesting that an increase in HCN1 channel expression contributes to the generation of absence seizures. Another study reported no change in HCN4 expression in the hippocampus following febrile seizures despite changes in HCN1. Loss-of-function mutations in HCN4 has also recently been associated with benign myoclonic epilepsy. More recently, increased HCN4 expression in the hippocampal dentate gyrus has been reported in individuals with SUDEP. However, it was unclear whether the alterations in increased HCN4 expression preceded seizure occurrence and were responsible for seizures. Patch clamp recordings in acute slices reported the abnormal expression of HCN currents in Rheb$^{CA}$ neurons as early as P8, about two weeks prior to the onset of convulsive seizures (observed starting at P21), In addition. HCN4 expression was not detected in the contralateral hemispheres lacking FCM, but experiencing epileptiform activity. These data suggest that HCN4 expression in neurons with hyperactive mTOR precedes seizures. Finally, clear causality between HCN4 activity and seizure occurrence was shown, as genetically blocking HCN4 activity prevented the development of seizures.

Identifying ectopic HCN4 has several important clinical implications. At the present time, there are no HCN blockers that are selective for HCN4. However, the findings herein support HCN4 as a prime candidate for shRNA-based gene therapy for treating seizures associated with FCDII and TSC that exhibit focal conical malformations. While ectopic HCN4 expression was eliminated with rapamycin treatment, directly targeting HCN4 for epilepsy treatment would prevent the severe adverse events that occur when using the higher rapamycin doses necessary to improve efficacy. Furthermore, considering that HCN4 is downstream of mTOR signaling, these findings are likely applicable to other mTORopathies resulting from mutations in the mTOR and GATOR pathway genes (e.g., AKT, PI3K, mTOR, RHEB, DEPDC5, NRPL2/3.

In conclusion, provided herein is an evidence that enlarged, dysmorphic mutant neurons in mouse and human FCMs express HCN4 channels that are normally absent in cortical neurons in young adults. This ectopic HCN4 channel expression is mTOR-dependent, precedes the development of epilepsy, and contributes to the generation of seizures by enhancing the excitability of FCM neurons. These findings add to the body of literature on HCN channels in epilepsy, and more importantly, highlight a novel mechanism of seizures by the unexpected contribution of the isoform 4 of HCN channels that has high cAMP-sensitivity. This mechanism can explain how sensory stimulations leading to the activation of specific cAMP-generating dopaminergic or adrenergic inputs onto FCM neurons would trigger seizures. In addition, the unique expression of HCN4 channels in dysmorphic FCM neurons provides a highly specific target for gene therapy for epilepsy treatment for individuals with TSC and FCDII.

Example 9: Gene Therapy Targeting of HCN4 for the Treatment of Epilepsy

To deliver shRNA against HCN4 or a control shRNA against luciferase, recombinant adeno-associated virus (AAV) are prepared encoding these shRNA. Several AAV serotypes e.g., AAV2 will be stereotactically injected into the cortex containing FCM. In addition, several titers ($10^{11}$ to $10^{14}$ viral particles per ml) are tested. 2 to 6 injections (0.5 µl) are performed at distinct locations (spaced by 200 to 500 µm) to cover the entire FCM in 1-2 month-old mice. In a subset of mice, patch clamp recordings are obtained 3 weeks-post-viral injections to examine whether HCN4 expression was decreased. Whole cell patch clamp recordings of h current are obtained and the current amplitudes are quantified. In another subset of AAV-injected mice, the EEG implants are placed after the last viral injections. If placing the EEG implants cannot be performed following the viral injections, they are added 2-3 weeks post-viral injection. About 3-6 weeks post viral injections, video-EEG recordings of the mice injected with either AAV-HCN4 shRNA or AAV-luciferase shRNA are obtained. Recordings are obtained for 7-14 days. Post-EEG recordings, animals will be sacrificed to prepare brain sections and immunostain for HCN4. AAV-driven HCN4 shRNA decreases HCN4 expression leading to a significant decrease in seizure frequency.

Example 10: Detecting Overexpression of HCN4 for the Diagnosis of FCDII and TSC

Developing a method to detect ectopic HCN4 expression in the cortex of TSC or FCDII patients would be useful for several reasons; it would further validate that these patients are good candidate for gene therapy; it would allow to delineate the FCM for surgical resection considering that the method used today MRI does not allow a clear definition of the FCM; it would also allow to quantify whether the gene therapy was successful. Positron emission tomography (PET) radiotracer that selectively binds HCN4 is used. The binding affinity of the ligand for generating the HCN4 PET tracer is tested in vitro in cultured neurons expressing GFP or Rheb$^{CA}$. Control cortical neurons do not express HCN4 allowing validation that the ligand has low or no binding affinity for normal cortical neurons. PET studies are performed in 2-month old mice containing FCM (generating with Rheb$^{CA}$ in utero electroporation at E15) and control mice (electroporated with GFP). FCM display significantly higher binding of HCN4 PET tracer than control mice and this provides high resolution imaging of the FCM neurons, allowing more precise surgery and facile diagnosis of these conditions.

TABLE 1

Patient information

| Patient # | Age | Sex | Type | Medical notes |
| --- | --- | --- | --- | --- |
| 1 (FIG. 6A) | 5 | Male | FCD IIb | Left superior frontal gyrus seizures, cortical dyslamination, dysmorphic neurons, balloon cells, and gliosis |
| 2 (FIG. 6B, FIGS. 15A-15E) | 31 | Female | FCDIIa | Left frontal gyrus seizures, cortical dyslamination, dysmorphic neurons. |
| 3 (FIG. 16A-16B) | 23 | Female | FCDIIa | Right superior frontal gyrus seizures, cortical dyslamination, dysmorphic neurons, |
| 4 (FIG. 16C-16D) | 28 | Male | FCDIIa | Left temporal seizures, cortical dyslamination, dysmorphic neurons. |
| 5 (FIG. 16E) | 40 | Male | FCDIIa | Left temporal seizures, cortical dyslamination, dysmorphic neurons. |

TABLE 1-continued

| | | Patient information | | |
|---|---|---|---|---|
| Patient # | Age | Sex | Type | Medical notes |
| 6 Dennis (FIG. 6D and E, FIG. 12) | 35 | Female | FCD IIa | Intractable Focal Impaired Awareness (FIA) seizures from right occipital temporal lobes, cortical dyslamination, dysmorphic neurons |
| 7 Dennis (FIG. 16) | 12 | Male | FCD IIa | Left frontal focal motor seizures intractable, cortical dyslamination, dysmorphic neurons |
| 8 (FIG. 7A-C, FIG. 13) | 4 | Female | TSC | Right frontal opercular tuber |
| 9 (FIG. 7D-E) | 21 | Female | TSC | Focal seizures, cortical tuber and subependymal nodules |

TABLE 2

| | | Constructs used. |
|---|---|---|
| Plasmid | IUE concentration (μg/μL) | Notes/Origin |
| pCAGGS-Rheb S16H (Rheb$^{CA}$) | 2.0; 1.5 (for FIG. 1) | Gift |
| pCAG-GFP | 1.0-4.0 (as noted in figure legend) | Addgene (catalog no. 11150) (2) |
| pCAG-tdTomato | 1.0 | Addgene (#83029) (3) |
| pCAG-Kir2.1-T2A-tdTomato | 2.0 | Addgene (#60598) (4) |
| pCAGEN-hHCN4-AYA (HCN4$^{NF}$) | 4.0 | Synthesized coding sequence for hHCN4 (AJ132429.1) with G480A/G482A mutations (5), inserted into EcoRI and XhoI sites of pCAGEN (Addgene; catalog no. 11160). |
| pCAGEN-hHCN4 | 2.0 | Subcloned hHCN4 from pcDNA3-hHCN4 (6) into EcoRI and XhoI sites of pCAGEN (Addgene; catalog no. 11160). |
| pcDNA3-hHCN4 | N/A | Gift |
| pCAGEN | N/A | Addgene (catalog no. 11160) |

TABLE 3

| | | Primary and Secondary antibodies | | |
|---|---|---|---|---|
| Antibody | Company | Catalog Number | Host animal | Concentration used in IHC or WB when specified |
| Primary | | | | |
| HCN1 | UC Davis/NIH NeuroMab | N70/28 (75-110) | Mouse | 1:750 |
| HCN2 | UC Davis/NIH NeuroMab | N71/37 (75-111) | Mouse | 1:750 |
| HCN3 | UC Davis/NIH NeuroMab | N141/28 (75-175) | Mouse | 1:750 |
| HCN4 | UC Davis/NIH NeuroMab | N114/10 (75-150) | Mouse | 1:750 1:250 (human) 1:1000 WB |
| HCN4 | Alomone Labs | APC-052 | Rabbit | 1:300-1:500 1:500-1:1000 WB |
| NeuN | EMD Millipore | ABN78 | Rabbit | 1:2000 |
| NeuN | EMD Millipore | MAB 377 | Mouse | 1:2000 |
| NF-L | Cell Signaling | C28E10 | Rabbit | 1:500 |
| NF-L | Abcam | ab134460 | Chicken | 1:1000 |
| pS6 (S240/244) | Cell Signaling | D68F8 | Rabbit | 1:4000 |
| SMI311 | Covance | SMI-311R | Mouse | 1:4000 |
| SMI32 (NfH) | Abcam | 8135 | Rabbit | 1:750 |
| β-actin | Cell Signaling | 4970 | Rabbit | 1:2000 WB |
| GAPDH | Cell Signaling | 5174 | Rabbit | 1:5000 WB |
| DAPI | Life Technologies | D1306 | | 1:36000 |

TABLE 3-continued

Primary and Secondary antibodies

| Antibody | Company | Catalog Number | Host animal | Concentration used in IHC or WB when specified |
|---|---|---|---|---|
| Secondary | | | | |
| α Mouse IgG Alexa Fluor 633 | Thermo Fisher Scientific | A-21052 | Goat | 1:1000 |
| α Mouse IgG Alexa Fluor 488 | Thermo Fisher Scientific | A-11001 | Goat | 1:1000 |
| α Mouse IgG Alexa Fluor 568 | Thermo Fisher Scientific | A-11004 | Goat | 1:1000 |
| α Mouse IgG Alexa Fluor 555 | Thermo Fisher Scientific | A28180 | Goat | 1:1000 |
| α Rabbit IgG Alexa Fluor 488 | Thermo Fisher Scientific | A-11034 | Goat | 1:1000 |
| α Rabbit IgG Alexa Fluor 555 | Thermo Fisher Scientific | A-31572 | Donkey | 1:1000 |
| α Rabbit IgG Alexa Fluor 647 | Thermo Fisher Scientific | A-31573 | Donkey | 1:1000 |
| α Chicken IgY Alexa Fluor 488 | Thermo Fisher Scientific | A-11039 | Goat | 1:1000 |
| α Chicken IgG Alexa Fluor 555 | Thermo Fisher Scientific | A-21437 | Goat | 1:1000 |
| α Chicken IgG Alexa Fluor 647 | Thermo Fisher Scientific | A-21449 | Goat | 1:1000 |

TABLE 4

Summary of statistical tests

| FIG. | Test | Statistical value | P value | n | Definition of n |
|---|---|---|---|---|---|
| FIG. 1 | | | | | |
| 1F, soma size | Student's t test, unpaired, two-tailed | t (19) = 23.14 | <0.0001 | 10 (GFP) 11 ($Rheb^{CA}$) | Number of mice |
| 1G, phospho-S6 | Student's t test, unpaired, two-tailed | t (6) = 5.994 | <0.001 | 4 (GFP) 4 ($Rheb^{CA}$) | Number of mice |
| FIG. 2 | | | | | |
| 2C, pS6 intensity | Student's t test, unpaired, two-tailed | t (11) = 1.118 | 0.287 | 6 ($Rheb^{CA}$) 7 ($Rheb^{CA}$ + Kir2.1) | Number of mice |
| 2C, cell size | Student's t test, unpaired, two-tailed | t (11) = 0.2957 | 0.773 | 6 ($Rheb^{CA}$) 7 ($Rheb^{CA}$ + Kir2.1) | Number of mice |
| 2D, Capacitance | Student's t test, unpaired, two-tailed | t (18) = 0.8511 | 0.406 | 10 ($Rheb^{CA}$) 10 ($Rheb^{CA}$ + Kir2.1) | Neurons from 3 mice ($Rheb^{CA}$) and 3 mice ($Rheb^{CA}$ + Kir2.1) |
| 2D, RMP | Student's t test, unpaired, two-tailed | t (18) = 3.0820 | 0.0064 | 10 (RhebCA) 10 ($Rheb^{CA}$ + Kir2.1) | Neurons from 3 mice ($Rheb^{CA}$) and 3 mice ($Rheb^{CA}$ + Kir2.1) |
| 2D, Conductance | Student's t test, unpaired, two-tailed | t (21) = 3.448 | 0.0024 | 12 ($Rheb^{CA}$) 11 ($Rheb^{CA}$ + Kir2.1) | Neurons from 5 mice ($Rheb^{CA}$) and 2 mice ($Rheb^{CA}$ + Kir2.1) |
| 2F, AP half-width | Student's t test, unpaired, two-tailed | t (25) = 0.00714 | 0.9944 | 12 ($Rheb^{CA}$) 15 ($Rheb^{CA}$ + Kir2.1) | Neurons from 5 mice ($Rheb^{CA}$) and 3 mice ($Rheb^{CA}$ + Kir2.1) |
| 2F, AP firing threshold | Student's t test, unpaired, two-tailed | t (23) = 0.5570 | 0.5825 | 12 ($Rheb^{CA}$) 13 ($Rheb^{CA}$ + Kir2.1) | Neurons from 5 mice ($Rheb^{CA}$) and 3 mice ($Rheb^{CA}$ + Kir2.1) |
| 2H | Two-way repeated measures ANOVA Sidak post-test | Interaction: $F_{(29, 580)}$ = 3.364, p < 0.0001 Row factor: $F_{(29, 580)}$ = 47.08, p < 0.0001 | 0.05 | 8 ($Rheb^{CA}$) 14($Rheb^{CA}$ + Kir2.1) | Neurons from 2 mice ($Rheb^{CA}$) and 3 mice ($Rheb^{CA}$ + Kir2.1) |

TABLE 4-continued

Summary of statistical tests

| FIG. | Test | Statistical value | P value | n | Definition of n |
|---|---|---|---|---|---|
| | | Column factor:<br>$F(1, 20) = 6.279$, $p = 0.0219$<br>Subjects (matching)<br>$F(20, 580) = 18.16$,<br>$p < 0.0001$ | | | |
| 2J, seizure duration | Student's t test, unpaired, two-tailed | $t(8) = 0.292$ | 0.7777 | 7 ($Rheb^{CA}$)<br>3 ($Rheb^{CA}$ + Kir2.1) | Number of mice |
| 2J, number of seizures per day | Mann Whitney U test, two-tailed | $U = 3$ | 0.0082 | 7 ($Rheb^{CA}$)<br>6 ($Rheb^{CA}$ + Kir2.1) | Number of mice |
| | | FIG. 3 | | | |
| 3A, RMP | Student's t test, unpaired, two-tailed | $t(45) = 12.15$ | <0.0001 | 26 (GFP)<br>21 ($Rheb^{CA}$) | Neurons from 5 mice (GFP) and 4 mice ($Rheb^{CA}$) |
| 3B, conductance | Student's t test, unpaired, two-tailed | $t(24) = 13.46$ | <0.0001 | 15 (GFP)<br>11 ($Rheb^{CA}$) | Neurons from 3 mice (GFP) and 3 mice ($Rheb^{CA}$) |
| 3D | Two-way repeated measures ANOVA Sidak post-test | From 0 to 600 pA injection:<br>Interaction:<br>$F(6, 90) = 23.61$, $P < 0.0001$<br>Row factor:<br>$F(6, 90) = 176.8$, $P < 0.0001$<br>Column factor:<br>$F(1, 15) = 32.92$, $P < 0.0001$<br>Subjects (matching)<br>$F(15, 90) = 10.76$,<br>$P < 0.0001$<br>From 600 to 1000<br>$F(3, 30) = 2.119$, $P = 0.1187$<br>$F(3, 30) = 129.4$, $P < 0.0001$<br>$F(1, 10) = 23.82$, $P = 0.0006$<br>$F(10, 30) = 117.1$, $P < 0.0001$ | 0.05 | From 0 to 600 pA injection<br>8 (GFP)<br>9 ($Rheb^{CA}$)<br>From 600 to 1000 pA injection<br>3 (GFP)<br>9 ($Rheb^{CA}$) | Neurons from 4 mice each condition |
| 3H | Two-way repeated measures ANOVA Tukey post-test | Interaction:<br>$F(18, 90) = 40.75$,<br>$p < 0.0001$<br>Row effect:<br>$F(9, 90) = 229.4$, $p < 0.0001$<br>Column effect:<br>$F(2, 10) = 26.61$, $p < 0.0001$<br>Subjects (matching):<br>$F(10, 90) = 9.292$,<br>$p < 0.0001$ | 0.05 | 5 (GFP)<br>5 ($Rheb^{CA}$)<br>3 ($Rheb^{CA}$ + Zatebradine) | Neurons from 2 mice (GFP),<br>4 mice ($Rheb^{CA}$), and<br>2 mice ($Rheb^{CA}$ + Zatebradine) |
| 3I, RMP ($Rheb^{CA}$ vs $Rheb^{CA}$ + Zatebradine) | Student's t test, unpaired, two-tailed | $t(16) = 8.294$ | <0.0001 | 11 ($Rheb^{CA}$)<br>7 ($Rheb^{CA}$ + Zatebradine) | Neurons from 3 mice (GFP) and 3 mice ($Rheb^{CA}$) |
| 3J | Two-way repeated measures ANOVA Tukey post-test | Interaction:<br>$F(18, 288) = 27.03$,<br>$p < 0.0001$<br>Row effect:<br>$F(9, 288) = 44.72$, $p < 0.0001$<br>Column effect:<br>$F(2, 32) = 31.71$, $p < 0.0001$<br>Subjects (matching):<br>$F(32, 288) = 14.43$,<br>$p < 0.0001$ | 0.05 | 8 (GFP)<br>20 ($Rheb^{CA}$)<br>7 ($Rheb^{CA}$ + Zatebradine) | Neurons from 2 mice (GFP),<br>4 mice ($Rheb^{CA}$), and<br>2 mice ($Rheb^{CA}$ + Zatebradine) |
| 3K | Pearson correlation | $r = -0.6887$ | 0.0008 | 20 | Neurons from 7 mice |
| 3M | Student's t test, paired, two-tailed | $t(8) = 4.16$ | 0.0032 | 9 (ACSF)<br>9 (Forskolin in ACSF)<br>8 (ACSF)<br>8 (Forskolin in ACSF) | $Rheb^{CA}$ neurons from 3 mice<br>GFP neurons from 3 mice |

TABLE 4-continued

Summary of statistical tests

| FIG. | Test | Statistical value | P value | n | Definition of n |
|---|---|---|---|---|---|
| FIG. 4 | | | | | |
| 4I | Student's t test, paired, two-tailed | t (4) = 66.91 | <0.0001 | 3 each | Mice (15 cells per mouse) |
| FIG. 5 | | | | | |
| 5C | Student's t test, paired, two-tailed | t (4) = 4.666 | 0.0095 | 3 each | Mice (8-10 cells per mouse) |
| 5D | Student's t test, paired, two-tailed | HCN1 t (9) = 0.02423<br>HCN2 t (9) = 0.7537<br>HCN4 t (9) = 0.8417<br>VEGF t (7) = 2.477 | 0.9812<br>0.4703<br>0.4217<br>0.0383 | 6 (GFP) and 5 ($Rheb^{CA}$) for HCNs and 5 and 5 for VEGF | Microdissected cortex containing electroporated cells |
| 5F | Two-way repeated measures ANOVA Tukey post-test | Interaction:<br>F (9, 180) = 35.26, p < 0.0001<br>Row effect:<br>F (9, 180) = 59.49, p < 0.0001<br>Column effect:<br>F (1, 20) = 39.64, p < 0.0001<br>Subjects (matching):<br>F (20, 180) = 10.79.<br>p < 0.0001 | 0.05 | 9 (GFP)<br>13 ($Rheb^{CA}$) | Neurons from 2 mice (GFP), 3 mice ($Rheb^{CA}$), |
| 5H | One-way ANOVA Tukey post-hoc | F (3, 77) = 64.23<br>P < 0.0001 | 0.042, GFPvs$Rheb^{CA}$ <0.99, GFP, <P12 vs >P28 0.0001, $Rheb^{CA}$, <P12 vs >P28 | 24 (<P12 GFP)<br>14 (>P28 GFP)<br>25 (<P12 $Rheb^{CA}$)<br>20 (>P28 $Rheb^{CA}$) | Each group from >3 mice |
| FIG. 8 | | | | | |
| 8B | Two-way repeated measures ANOVA Sidak post-test | Interaction:<br>F (9, 153) = 62, p < 0.0001<br>Row factor:<br>F (9, 153) = 106, p < 0.0001<br>Column factor:<br>F (1, 17) = 100.1, p < 0.0001<br>Subjects (matching)<br>F (17, 153) = 9.188,<br>p < 0.0001 | 0.05 | 8 ($Rheb^{CA}$)<br>11 ($Rheb^{CA}$ + $HCN4^{NF}$) | Neurons from 4 mice ($Rheb^{CA}$)<br>3 mice ($Rheb^{CA}$ + $HCN4^{NF}$) |
| 8G, RMP | Student's t test, unpaired, two-tailed | t (21) = 7.412 | <0.0001 | 12 ($Rheb^{CA}$)<br>11 ($Rheb^{CA}$ + $HCN4^{NF}$)<br>26 (control from FIG. 2) | Neurons from 4 mice ($Rheb^{CA}$) and 3 mice ($Rheb^{CA}$ + $HCN4^{NF}$) |
| 8E, pS6 intensity | Student's t test, unpaired, two-tailed | t (13) = 0.08209 | 0.9358 | 7 ($Rheb^{CA}$)<br>8 ($Rheb^{CA}$ + $HCN4^{NF}$) | Number of mice |
| 8E, soma size | Student's t test, unpaired, two-tailed | t (12) = 1.534 | 0.1510 | 7 ($Rheb^{CA}$)<br>7 ($Rheb^{CA}$ + $HCN4^{NF}$) | Number of mice |
| 8F, AP half-width | Student's t test, unpaired, two-tailed | t (2) = 0.5903 | 0.5616 | 12 ($Rheb^{CA}$)<br>10 ($Rheb^{CA}$ + $HCN4^{NF}$) | Neurons from 4 mice ($Rheb^{CA}$) and 3 mice ($Rheb^{CA}$ + $HCN4^{NF}$) |
| 8F, AP firing threshold | Student's t test, unpaired, two-tailed | t (20) = 2.011 | 0.0580 | 12 ($Rheb^{CA}$)<br>10 ($Rheb^{CA}$ + $HCN4^{NF}$) | Neurons from 4 mice ($Rheb^{CA}$) and 3 mice ($Rheb^{CA}$ + $HCN4^{NF}$) |
| 8H | Two-way repeated measures ANOVA Sidak post-test | Interaction:<br>F (29, 551) = 2.276.<br>p = 0.0002<br>Row factor:<br>F (29, 580) = 371.2,<br>p < 0.0001<br>Column factor:<br>F (1, 19) = 2.905, p = 0.1046<br>Subjects (matching)<br>F (19, 551) = 23.65,<br>p < 0.0001 | 0.05 | 11 ($Rheb^{CA}$)<br>10 ($Rheb^{CA}$ + $HCN4^{NF}$) | Neurons from 3 mice ($Rheb^{CA}$) and 3 mice ($Rheb^{CA}$ + $HCN4^{NF}$) |
| 8J | Mann Whitney U test | U = 0 | 0.0006 | 7 ($Rheb^{CA}$)<br>7 ($Rheb^{CA}$ + $HCN4^{NF}$) | Number of mice |

TABLE 4-continued

Summary of statistical tests

| FIG. | Test | Statistical value | P value | n | Definition of n |
|---|---|---|---|---|---|
| FIGS. | | | | | |
| FIGS. 9A-9B | Two-way repeated measures ANOVA Sidak post-test | Interaction: $F (9, 234) = 8.988, p < 0.0001$ Row factor: $F (9, 234) = 88.68, p < 0.0001$ Column factor: $F (1, 26) = 7.072, p = 0.0132$ Subjects (matching) $F (26, 234) = 14.99, p < 0.0001$ | 0.05 | 8 (Rheb$^{CA}$, 1.5 μg/μl) 20 (Rheb$^{CA}$, 2 μg/μl) | Neurons from 2 mice (Rheb$^{CA}$, 1.5 μg/μl) and 4 mice (Rheb$^{CA}$, 2 μg/μl, used in FIG. 2e) |
| FIG. 17C Sonia size | Student's t test, unpaired, two-tailed | $t (10) = 0.1773$ | 0.8628 | 6 each | Number of mice (GFP and HCN4) |
| FIG. 17C Phospho-S6 | Student's t test, unpaired, two-tailed | $t (10) = 0.1452$ | 0.8875 | 6 each | Number of mice (GFP and HCN4) |
| FIG. 17E | Two-way repeated measures ANOVA Sidak post-test | Interaction: $F (9, 198) = 3.414, p < 0.0006$ Row factor: $F (9, 198) = 44.11, p < 0.0001$ Column factor: $F (1, 22) = 4.787, p = 0.0396$ Subjects (matching) $F (22, 198) = 14.89, p < 0.0001$ | 0.05 | 6 (GFP) and 18 (HCN4) | Neurons from 2 mice (GFP) and 3 mice (HCN4) |
| FIG. 17F | Student's t test, unpaired, two-tailed | $t (24) = 7.052$ | <0.0001 | 8 (GFP) and 18 (HCN4) | Neurons from 3 mice (GFP) and 3 mice (HCN4) |
| FIG. 17H | Two-way repeated measures ANOVA Sidak post-test | Interaction: $F (18, 288) = 2.211, p = 0.0035$ Row factor: $F (18, 266) = 345.6, p < 0.0001$ Column factor: $F (1, 16) = 4.282, p = 0.0551$ Subjects (matching) $F (16, 288) = 81.76, p < 0.0001$ | 0.05 | 8 each | Neurons from 3 mice (GFP) and 3 mice (HCN4) |

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating epilepsy in a subject in need thereof, the method comprising contacting a target cell of the subject with an effective amount of an HCN4 disrupting agent, wherein the HCN4 disrupting agent is an adenoviral vector comprising a polynucleotide encoding HCN4$^{NF}$, and wherein the HCN4$^{NF}$ comprises the mutations G480A and G482A relative to the sequence set forth in SEQ ID NO: 1.

2. The method of claim 1, wherein the HCN4 disrupting agent is encapsulated in liposome-templated hydrogel nanoparticles (LHNPs).

3. The method according to claim 1, wherein the target cell is a focal-cortical malformation (FCM) neuron.

4. The method according to claim 3, wherein the HCN4 disrupting agent is locally administered to the FCM neuron.

5. The method of claim 1, wherein the epilepsy comprises an mTORopathy.

6. The method of claim 1, wherein the epilepsy is focal-cortical dysplasia type II (FCDII) or tuberous sclerosis complex (TSC).

7. The method of claim 1, wherein the epilepsy results from Cowden syndrome, brain trauma, genetic disorders due to mutations in PI3K-AKT-mTOR gene pathways or in a GATOR gene pathway, or brain tumors.

8. The method according to claim 5, wherein the mTORopathy is mTOR hyperactivity.

\* \* \* \* \*